United States Patent [19]

Belliotti et al.

[11] Patent Number: 5,075,330

[45] Date of Patent: Dec. 24, 1991

[54] N-HYDROXYAMIDE, N-HYDROXYTHIOAMIDE, N-HYDROXYUREA, AND N-HYDROXYTHIOUREA DERIVATIVES OF SELECTED NSAIDS AS ANTIINFLAMMATORY AGENTS

[75] Inventors: Thomas R. Belliotti, Ypsilanti; Wiaczeslaw A. Cetenko; David T. Connor, both of Ann Arbor, all of Mich.; Daniel L. Flynn, Mundelein, Ill.; Catherine R. Kostlan, Saline, Mich.; James B. Kramer, Sylvania, Ohio; Jagadish C. Sircar, Ann Arbor, Mich.

[73] Assignee: Warner-Lambert Co., Morris Plains, N.J.

[21] Appl. No.: 598,471

[22] Filed: Oct. 16, 1990

Related U.S. Application Data

[62] Division of Ser. No. 358,323, May 26, 1989, Pat. No. 4,981,865.

[51] Int. Cl.$^5$ ................ C07D 313/12; A61K 31/335
[52] U.S. Cl. .................................. 514/450; 549/354
[58] Field of Search ................ 549/354; 514/450

[56] References Cited

U.S. PATENT DOCUMENTS 4,769,387  9/1988  Summers et al. .................. 514/468

FOREIGN PATENT DOCUMENTS

| | | |
|---|---|---|
| 0196674 | 8/1986 | European Pat. Off. . |
| 0196184 | 10/1986 | European Pat. Off. . |
| 0279263 | 8/1988 | European Pat. Off. . |
| 0279281 | 8/1988 | European Pat. Off. . |
| 0292699 | 11/1988 | European Pat. Off. . |
| 2191194 | 12/1987 | United Kingdom . |
| 2194531 | 3/1988 | United Kingdom . |

OTHER PUBLICATIONS

J. Org. Chem., vol. 54, No. 5, 1989, 1221-1223, A. O. Stewart et al.
J. Med. Chem., 1988, vol. 31, 3-5, J. B. Summers et al.
J. Med. Chem., 1987, 30, 574-580, J. B. Summers et al.

*Primary Examiner*—Mary C. Lee
*Assistant Examiner*—Lenora Miltenberger
*Attorney, Agent, or Firm*—Joan Thierstein

[57] ABSTRACT

The present invention includes N-hydroxyamide, N-hydroxyurea, N-hydroxythioamide, and N-hydroxythiourea derivatives of fenamates, indomethacin, cicloprofen, oxepinac, and indoprofen as dual inhibitors or selective ihibitors of cyclooxygenase and 5-lipoxygenase.

9 Claims, No Drawings

N-HYDROXYAMIDE, N-HYDROXYTHIOAMIDE, N-HYDROXYUREA, AND N-HYDROXYTHIOUREA DERIVATIVES OF SELECTED NSAIDS AS ANTIINFLAMMATORY AGENTS

This is a divisional application of U.S. Ser. No. 07/358,323 filed May 26, 1989, now U.S. Pat. No. 4,981,865.

BACKGROUND OF THE INVENTION

The present invention is novel compounds which are N-hydroxyamide, N-hydroxyurea, N-hydroxythioamide and N-hydroxythiourea derivatives of fenamate, indomethacin, cycloprofen, oxapinac and indoprofen, and pharmaceutically acceptable acid addition or base salts thereof, pharmaceutical compositions and methods of use therefor. The invention compounds are now found to have activity as dual inhibitors or selective inhibitors of 5-lipoxygenase and cyclooxygenase providing treatment of conditions advantageously affected by such inhibition including inflammation, arthritis, pain, fever, and the like. Thus, the present invention is also a pharmaceutical composition or method of use therefor.

Specific hydroxamates of fenamic acid are shown in copending U.S. application Ser. No. 134,725 which includes a reference to European Application Publication No. 0,196,184 having broad disclosure of hydroxamic acid derivatives of selected aryl ring systems effective as high potency inhibitors of 5-lipoxygenase. Summers et al also disclosed hydroxamic acid inhibitors of 5-lipoxygenase in an abstract, September, 1987 and *J. Med. Chem.*, 1987, 30, 574-80. Indole, benzofuran and benzothiophine each having an —A—N—C—R₁ substituent is disclosed in European Application Publication No. 0279,263. Additionally various ring systems are known which are attached to a similar N—C containing substituent. For example, a (phenylalkoxy) phenyl; a biphenyl alkyl; a phenyl or naphthyl; 7-oxabicyclo (2.2.1) heptane; dibenzofuran; and (alkoxy) or (phenyloxy)-phenyl and naphthyl or thiofurane are disclosed in European Application Publication No. 279,281, British No. 2,191,194, PCT Application No. GB 86/00791 British No. 2,194,531, U.S. Pat. No. 4,769,387, and European Application Publication No. 292,699 respectively. European Application Publication No. 196,674 also discloses compounds including an -N-C- containing moiety having phenyl, naphthyl or sulfur heterocyclic ring systems attached directly or through various linking groups to the N of the moiety. The *J. Org. Chem.* 1989, 54, 1221-1223 and *J. Med. Chem.*, 31, 1, pp. 3-5 (Jan. 1988) disclose (hydroxy) or phenylalkoxy)-phenyl, naphthyl and phenoxyphenyl rings in like manner attached to an —N—C— containing substituent.

However, none of the above noted disclosures describe hydroxamates of the configuration disclosed in this application on the selected nonsteroidal antiinflammatory type substrates.

Thus, the differences between the present invention and the teachings of the references are readily apparent.

SUMMARY OF THE INVENTION

The present invention is a compound of the formula (I)

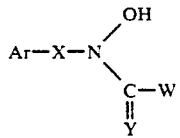

and a pharmaceutically acceptable acid addition or base salt thereof; wherein

Ar is

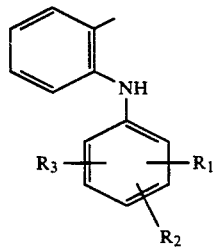

wherein R₁, R₂ and R₃ are independently H, fluoro, chloro, bromo, iodo, CF₃, lower alkyl, CN, hydroxy, lower alkoxy, —S(O)$_q$—lower alkyl, NO₂, or NR₄R₅ wherein R₄ or R₅ are independently H, lower alkyl or acyl and q is an integer of 0, 1 or 2;

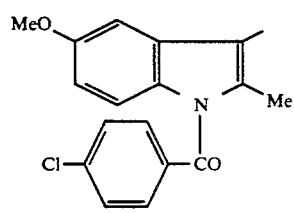

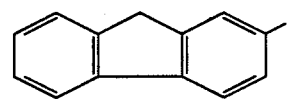

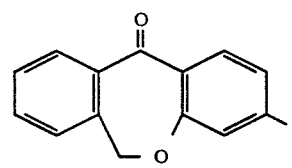

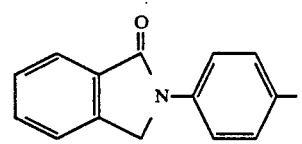

X is CH₂,

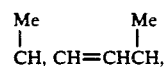

or CH=CHCH₂;

Y is O or S;

W is alkyl, aryl, aralkyl, 0-alkyl, NR₆R₇, (CH₂)$_n$CO₂R₇, NH(CH₂)$_m$CO₂R₇, NH(CH₂)$_p$NR₆R₇, NHCH₂CH=CH₂ wherein (i) R₆ and R₇ are independently H or lower alkyl, (ii) n is 0 to 3 except that Y cannot be S when n is 0, (iii) m is 0 to 3,
and (iv) p is 2 to 3.

Additionally, the present invention is for novel compounds of the formula (II and IIa).

N-Hydroxy-9H-fluorene-2-methanamine     II,

N-Hydroxy-alpha-methyl-9H-fluorene-2-methanamine     IIa and the pharmaceutically acceptable acid addition or base salt of each.

The compounds of formula II and IIa are useful as intermediates in a process for the preparation of selected compounds of the formula I and also each is active as a dual inhibitor or selective inhibitor of 5-lipoxygenase and cyclooxygenase.

The present invention is also a pharmaceutical composition for the treatment of a condition advantageously affected by the dual inhibition or selective inhibition of 5-lipoxygenase and cyclooxygenase which comprises an amount effective for the treatment of the condition comprising a compound of the formula I and the pharmaceutically acceptable acid addition or base salt thereof or a compound of the formula II, IIa and the pharmaceutically acceptable salts of each, together with a pharmaceutically acceptable carrier. The "condition" is meant to include, for example, inflammation, arthritis or other inflammatory diseases, allergies, pain, fever, and psoriasis, but preferably inflammation.

The present invention is also a method for treatment of the condition as noted above in mammals, including humans, suffering therefrom with a compound of the formula I or the pharmaceutically acceptable acid addition or base salt thereof, or a compound of the formula II or IIa and the pharmaceutically acceptable salt thereof, in unit dosage form. The invention also provides for use of any such compound of formula I or salt thereof or of formula II or IIa or salt thereof in the manufacture of medical therapeutical agent.

Pharmaceutical composition or use of the compound or salt of formula I or of the compound or salt of formula II or IIa is meant to include treatment understood to be prophylactic pertinent to the foregoing named condition.

The preferred compounds of the present invention are of the formula I and in the present invention include:

N-[[2-[(2,6-dichloro-3-methylphenyl)amino]phenyl]methyl]-N-hydroxyacetamide

N-[[2-[(2,6-dichloro-3-methylphenyl)amino]phenyl]methyl]-N-hydroxyacetamide, monosodium salt N-hydroxy-N-[[2-[[3-(trifluoromethyl)phenyl]amino]phenyl]methyl]acetamide N-hydroxy-N-[[2-[[3-(trifluoromethyl)phenyl]amino]phenyl]methyl]acetamide, monosodium salt 1-(4-chlorobenzoyl)-N-hydroxy-5-methoxy-2-methyl-N-[(methylamino) thioxomethyl]-1H-indole-3-methanamine N-hydroxy-N'-methyl-N-[[2-[[3-(trifluoromethyl)phenyl]amino]phenyl]methyl]urea N-[(6,11-dihydro-11-oxodibenz[b,e]oxepin-3-yl) methyl]-N-hydroxy-2-methylpropanamide N-hydroxy-N-[[2-[[3-(trifluoromethyl)phenyl]amino]phenyl]methyl]carbamic acid, ethyl ester N-[1-[1-(4-chlorobenzoyl)-5-methoxy-2-methyl-1H-indol-3-yl]ethyl]-N-hydroxyacetamide.

The most preferred compound of formula I in the present invention is N-[[2-[(2,6-dichloro-3-methylphenyl)amino]phenyl]methyl]-N-hydroxyacetamide.

DETAILED DESCRIPTION OF THE INVENTION

In the compounds of formula (I) the term "lower alkyl" includes an alkyl group of from one to six carbons such as methyl, ethyl, propyl, butyl, and the like and isomers thereof. Halogen is chloro, bromo or fluoro. Further, the term "lower alkoxy" is of from one to six carbons such as methoxy, ethoxy, propoxy, butoxy and the like and isomers thereof. Likewise, acyl is of from two to six carbons including acetyl, propionyl, butyryl, and the like and isomers thereof.

Me is methyl, Et is ethyl and iPr is isopropyl.

Aryl is phenyl unsubstituted or substituted by halo, nitro, cyano, lower alkyl, lower alkoxy or trifluoromethyl.

Aralkyl is an aryl as defined above attached through an alkylenyl of from one to four carbons.

Appropriate compounds of formula I or II and IIA are useful in the free base form, in the form of base salts where possible, and in the form of acid addition salts. The three forms are within the scope of the invention. In practice, use of the salt form amounts to use of the base form. Pharmaceutically acceptable salts within the scope of the invention may be those derived from mineral acids such as hydrochloric acid and sulfuric acid; and organic acids such as ethanesulfonic acid, benzenesulfonic acid, p-toluenesulfonic acid, and the like, giving the hydrochloride, sulfate, ethanesulfonate, benzenesulfonate, p-toluenesulfonate and the like, respectively, or those derived from bases such as suitable organic and inorganic bases. Examples of pharmaceutically acceptable base addition salts with compounds of the present invention include organic bases which are nontoxic and strong enough to form such salts. These organic bases form a class whose limits are readily understood by those skilled in the art. Merely for purposes of illustration, the class may be said to include mono-, di-, and trialkylamines such as methylamine, dimethylamine, and triethylamine; mono-, di-, or trihydroxyalkylamines such as mono-, di-, or triethanolamine; amino acids such as arginine and lysine; guanidine; N-methylglucosamine; N-methylglucamine; L-glutamine; N-methylpiperazine; morpholine; ethylenediamine; N-benzylphenethylamine; tris(hydroxymethyl) aminomethane; and the like. (See for example, "Pharmaceutical Salts," *J. Pharm. Sci.*, 66(1):1–19 (1977).) Salts of inorganic bases include sodium, potassium, calcium or the like.

The acid addition salts of said basic compounds are prepared either by dissolving the free base or acid of compound I or II and IIa in aqueous or aqueous alcohol solution or other suitable solvents containing the appropriate acid or base and isolating the salt by evaporating the solution, or by reacting the free base of compound I or II and IIa with an acid as well as reacting compound I having an acid group thereon with a base such that the reactions are in an organic solvent, in which case the salt separates directly or can be obtained by concentration of the solution. Salts can also be prepared by adding base to an aqueous alcohol solution of another salt.

The compounds of the invention may contain geometric isomers. Thus, the invention includes the individual isomers and mixtures thereof. The individual isomers may be prepared or isolated by methods known in the art.

In determining when a lipoxygenase, cyclooxygenase, or dual lipoxygenase/cyclooxygenase inhibitor is indicated, of course inter alia, the particular condition in question and its severity, as well as the age, sex, weight, and the like of the subject to be treated, must be taken into consideration and this determination is within the skill of the attendant physician.

For medical use, the amount required of a compound of formula I or pharmacologically acceptable salt thereof or II and IIa or pharmacologically acceptable salt thereof to achieve a therapeutic effect will, of course, vary both with the particular compound, the route of administration, the mammal under treatment, and the particular disorder or disease concerned. A suitable dose of a compound of formula I or pharmacologically acceptable salt thereof or II and IIa or pharmacologically acceptable salt thereof for a mammal suffering from, or likely hereinbefore is 0.1 µg–500 mg of the compound per kilogram body weight per day. In the case of systemic administration, the dose may be in the range of 0.5 to 500 mg of the compound per kilogram body weight, the most preferred dosage being 0.5 to 50 mg/kg of mammal body weight administered two or three times daily. In the case of topical administration, e.g., to the skin or eye, a suitable dose may be in the range 0.1 ng–100 µg of the compound per kilogram, typically about 0.1 µg/kg.

In the case of oral dosing for the treatment or prophylaxis of arthritis or inflammation in general, due to any course, a suitable dose of a compound of formula I or II and IIa or physiologically acceptable salt thereof, may be as specified in the preceding paragraph, but most preferably is from 1 mg to 10 mg of the compound per kilogram, the most preferred dosage being from 1 mg to 5 mg/kg of mammal body weight, for example from 1 to 2 mg/kg.

It is understood that the ordinarily skilled physician or veterinarian will readily determine and prescribe the effective amount of the compound to prevent or arrest the progress of the condition for which treatment is administered. In so proceeding, the physician or veterinarian could employ relatively low doses at first, subsequently increasing the dose until a maximum response is obtained.

While it is possible for an active ingredient to be administered alone, it is preferable to present it as a pharmaceutical formulation comprising a compound of formula I or II and IIa or a pharmacologically acceptable acid addition or base salt thereof and a pharmacologically acceptable carrier therefor. Such formulations constitute a further feature of the present invention.

The formulations, both for veterinary and for human medical use, of the present invention comprise an active ingredient in association with a pharmaceutically acceptable carrier therefor and optionally other therapeutic ingredient(s). The carrier(s) must be 'acceptable' in the sense of being compatible with the other ingredients of the formulations and not deleterious to the recipient thereof.

The formulations include those in a form suitable for oral, pulmonary, ophthalmic, rectal, parenteral (including subcutaneous, intramuscular, and intravenous), intraarticular, topical, nasal, or buccal administration. Such formulations are understood to include long-acting formulations known in the art.

The formulations may conveniently be presented in unit dosage form and may be prepared by any of the methods well-known in the art of pharmacy. All methods may include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units such as capsules, cachets, tablets, or lozenges, each containing a predetermined amount of the active ingredient; in the form of a powder or granules; in the form of a solution or a suspension in an aqueous liquid or nonaqueous liquid; or in the form of an oil-in-water emulsion or a water-in-oil emulsion. The active ingredient may also be in the form of a bolus, electuary, or paste.

The usefulness of the compounds of the present invention as inhibitors of the 5-lipoxygenase enzyme, cyclooxygenase, or in treating related diseases or conditions may be demonstrated by their effectiveness in various standard test procedures. A description of each procedure follows.

ARBL/ARBC Whole Cell 5-Lipoxygenase and Cyclooxygenase Assays

Materials

The rat basophilic leukemia cell line (RBL-1) was obtained from the American Type Culture Collection (Rockville, Md.).

Radioimmunoassay (RIA) kits of $LTB_4$ and $PGF_{2\alpha}$ were obtained from Amersham (Arlington Heights, Ill.) and Seragen (Boston, Mass.), respectively.

All tissue culture media were obtained from GIBCO (Grand Island, N.Y.).

Method

RBL-1 cells are grown in suspension culture in Eagle's minimum essential medium supplemented with 12% fetal bovine serum at 37° C. in an incubator supplied with air-5% carbon dioxide. Cells are harvested by centrifugation. They are washed with cold phosphate buffered saline pH 7.4 (PBS; NaCl, 7.1 g; $Na_2HPO_4$, 1.15 g; $KH_2PO_4$, 0.2 g; and KCl, 0.2 g/l). Cells are finally suspended in PBS containing 1.0 mM calcium at a density of $2 \times 10^6$ cells/ml. Cells are incubated with and without test agent (in DMSO) (1% DMSO is without effect on arachidonic acid metabolism) for ten minutes at room temperature. Calcium ionophore A23187 (5 µM) is added and cells are incubated for seven minutes at 37° C. The reaction is stopped by chilling the tubes on ice for ten minutes. Cells are separated by centrifugation and the supernatant is stored at $-20°$ C. Aliquots (100 µl) are analyzed for $LTB_4$ and $PGF_{2\alpha}$ using radioimmunoassay kits as provided by the supplier.

Tables 1–4 contain biochemical data obtained from this whole cell assay either as $IC_{50}$s which are calculated as the amount of test compound causing 50% inhibition of $LTB_4$ or $PGF_{2\alpha}$ formation or % inhibition of $LTB_4$ or $PGF_{2\alpha}$ at the indicated amount expressed as µm.

TABLE 1

| Example | C(Y)W | R | ARBL IC$_{50}$ ($\mu$M) or % Inhibitors @ $\mu$M | ARBC IC$_{50}$ ($\mu$M) or % Inhibitors @ $\mu$M |
|---|---|---|---|---|
| 1 | H | H | 97% @ 16[a] | 76% @ 16[b] |
| 3 | C(O)COOH | H | N[c] | N[c] |
| 4 | C(O)Me | H | 100% @ 16[a] | 12 |
| 2 | C(O)COOEt | H | 96% @ 16[a] | N[c] |
| 5 | C(O)iPr | H | 99% @ 16[a] | N[c] |
| 6 | C(O)NHME | H | 100% @ 16[a] | N[c] |
| 7 | H | Me | 100% @ 16[a] | 89% @ 16[b] |
| 8 | C(O)NHMe | Me | 0.91 | N[c] |
| 9 | C(O)NHEt | Me | 100% @ 16[a] | 49% @ 16[b] |
| 11 | C(O)Me | Me | 0.76 | N[c] |
| 10 | C(S)NHMe | Me | 100% @ 16[a] | 59% @ 16[b] |
| 12 | C(O)OEt | Me | 95% @ 16[a] | 79% @ 16[b] |
| 13 | C(O)i-Pr | Me | 90% @ 16[a] | N[c] |
| 14 | C(S)NHEt | Me | 56% @ 0.25[a] | N[c] |

[a] % inhibition of LTB$_4$ at 16 $\mu$M or 0.25 $\mu$M.
[b] % inhibition of PGF$_{2\alpha}$ at 16 $\mu$M.
[c] Less than 40% inhibition at 16 $\mu$M.

TABLE 2

| Example | X | C(Y)W | ARBL IC$_{50}$ ($\mu$M) or % inhibition @ $\mu$M | ARBC IC$_{50}$ ($\mu$M) or % inhibition @ $\mu$M |
|---|---|---|---|---|
| 20 | —CH$_2$ | —C(O)—NHMe | 0.51 | N[c] |
| 18 | —CH$_2$ | —C(O)—CH$_3$ | 0.84 | N[c] |
| 19 | —CH$_2$ | —C(O)—COEt | 84% @ 16[a] | N[c] |
| 17 | —CH$_2$ | —C(O)-iPr | 100% @ 16[a] | 5.8 |

[a] % inhibition of LTB$_4$ at 16 $\mu$M.
[c] Less than 40% inhibition at 16 $\mu$M.

TABLE 3

| Example | R | R$_1$/R$_2$ | W | ARBL IC$_{50}$ ($\mu$M) or % inhibition @ $\mu$M | ARBC IC$_{50}$ ($\mu$M) or % inhibition @ $\mu$M |
|---|---|---|---|---|---|
| 54 | H | 2,6-diCl,3-Me | Me | 0.18 | 5.0 |
| 53 | Me | 2,6-diCl,3-Me | Me | 1.8 | N @ 32[c] |
| 47 | H | 2,3-diMe | Me | 0.51 | 15 |
| 55 | H | 3-CF$_3$ | Me | 0.28 | 5.2 |
| 48 | H | 2,6-diCl | Me | 1.3 | N @ 32[c] |
| 56 | H | 3-CF$_3$ | NHMe | 0.12 | 2.2 |
| 57 | H | 3-CF$_3$ | OEt | 100% @ 16[a] | 91% @ 16[b] |

[a] % inhibition of LTB$_4$ at 16 $\mu$M.
[b] % inhibition of PGF$_{2\alpha}$ at 16 $\mu$M.
[c] Less than 40% inhibition at 32 $\mu$M.

TABLE 4

| Example | Y | W | ARBL IC$_{50}$ ($\mu$M) or % inhibition @ $\mu$M | ARBC IC$_{50}$ ($\mu$M) or % inhibition @ $\mu$M |
|---|---|---|---|---|
| 63 | O | —Me | 1.4 | 15 |
| 64 | O | —CH$_2$COOEt | 1.1 | 14 |
| 69 | O | —NHMe | 2.5 | N[c] |
| 65 | O | —(CH$_2$)$_2$COOMe | 1.3 | 9.4 |
| 67 | O | —OMe | 97% @ 32[a] | 16 |
| 74 | S | —NHMe | 0.40 | 7.1 |
| 68 | O | —NH$_2$ | 98% @ 16[a] | N[c] |
| 66 | O | —(CH$_2$)$_2$COOH | N @ 16[c] | N[c] |
| 72 | O | —NH—COOEt | 98% @ 16[a] | N[c] |
| 73 | O | NHCH$_2$CO$_2$Et | 100% @ 16[a] | N[c] |
| 71 | O | NHCH$_2$CH=CH$_2$ | 100% @ 16[a] | 50% @ 16[b] |
| 70 | O | NMe$_2$ | 100% @ 16[a] | 73% @ 16[b] |

[a] % inhibition of LTB$_4$ at 16 $\mu$M.
[b] % inhibition of PGF$_2$ at 16 $\mu$M.
[c] Less than 40% inhibition.

Accordingly, the present invention is for a compound of the formula I, II or IIa or pharmaceutically acceptable salts thereof, and a pharmaceutical composition or method of use, therefor, having usefulness in treating conditions advantageously inhibiting 5-lipoxygenase or cyclooxygenase such as outlined above:

In addition to the compounds of formula I or II and IIa, the pharmaceutical compositions can also contain other active ingredients, such as cyclooxygenase inhibitors, nonsteroidal antiinflammatory drugs (NSAIDS), peripheral analgesic agents such as zomepirac, diflunisal, and the like. The weight ratio of the compound of the formula I or II and IIa to the second active ingredient may be varied and will depend upon the effective dose of each ingredient. Generally, an effective dose of each will be used. Thus, for example, when a compound of the formula I or II and IIa is combined with an NSAID, the weight ratio of the compound of the formula I or II and IIa to the NSAID will generally range from about 1000:1 to about 1:1000, preferably about 200:1 to about 1:200. Combinations of a compound of the formula I or II and IIa and other active ingredients will generally also be within the aforementioned range, but in each case, an effective dose of each active ingredient should be used.

Combinations of a compound of the formula I and other active ingredients will generally be in the aforementioned ratios.

NSAIDS can be characterized into five groups:
(1) the propionic acid derivatives;
(2) the acetic acid derivatives;
(3) the fenamic acid derivatives;
(4) the biphenylcarboxylic acid derivatives; and
(5) the oxicams
or a pharmaceutically acceptable salt thereof.

The propionic acid derivatives which may be used comprise: ibuprofen, ibuprofen aluminum, indoprofen, ketoprofen, naproxen, benoxaprofen, flurbiprofen, fenoprofen, fenbufen, pirprofen, carprofen, oxaprozin, pranoprofen, miroprofen, tioxaprofen, suprofen, alminoprofen, tiaprofen, fluprofen, and bucloxic acid. Structurally related propionic acid derivatives having similar analgesic and antiinflammatory properties are also intended to be included in this group.

Thus, "propionic acid derivatives" as defined herein are nonnarcotic analgesics/nonsteroidal antiinflammatory drugs having a free —CH(CH$_3$)COOH or —XH$_2$CH$_2$COOH group (which optionally can be in the form of a pharmaceutically acceptable salt group, e.g., —CH(CH$_3$)COO$^-$Na$^+$ or —CH$_2$CH$_2$COO$^-$Na+), typically attached directly or via a carbonyl function to a ring system, preferably to an aromatic ring system.

The acetic acid derivatives which may be used comprise: indomethacin, which is a preferred NSAID, sulindac, tolmetin, zomepirac, diclofenac, fenclofenac, alclofenac, ibufenac, isoxepac, furofenac, tiopinac, zidometacin, acematacin, fentiazac, clidanac, oxpinac, and fenclozic acid. Structurally related acetic acid derivatives having similar analgesic and antiinflammatory properties are also intended to be encompassed by this group.

Thus, "acetic acid derivatives" as defined herein are nonnarcotic analgesics/nonsteroidal antiinflammatory drugs having a free —CH$_2$COOH group (which optionally can be in the form of a pharmaceutically acceptable salt group, e.g. —CH$_2$COO$^-$Na$^+$), typically attached directly to a ring system, preferably to an aromatic or heteroaromatic ring system.

The fenamic acid derivatives which may be used comprise: mefanamic acid, meclofenamic acid, flufenamic acid, niflumic acid, and tolfenamic acid. Structurally related fenamic acid derivatives having similar analgesic and antiinflammatory properties are also intended to be encompassed by this group.

Thus, "fenamic acid derivatives" as defined herein are nonnarcotic analgesics/nonsteroidal antiinflammatory drugs which contain the basic structure:

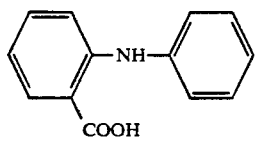

which can bear a variety of substituents and in which the free —COOH group can be in the form of a pharmaceutically acceptable salt group, e.g., —COO$^-$Na$^+$.

The biphenylcarboxylic acid derivatives which can be used comprise: diflunisal and flufenisal. Structurally related biphenylcarboxylic acid derivatives having similar analgesic and antiinflammatory properties are also intended to be encompassed by this group.

Thus, "biphenylcarboxylic acid derivatives" as defined herein are nonnarcotic analgesics/ nonsteroidal antiinflammatory drugs which contain the basic structure:

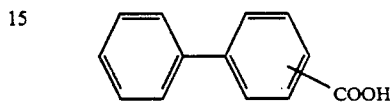

which can bear a variety of substituents and in which the free —COOH group can be in the form of a pharmaceutically acceptable salt group, e.g., —COO—Na$^+$.

The oxicams which can be used in the present invention comprise: piroxicam, sudoxicam, isoxicam, and 4-hydroxy-1,2-benzothiazine 1,1-dioxide 4-(N-phenyl)-carboxamide. Structurally related oxicams having similar analgesic and antiinflammatory properties are also intended to be encompassed by this group.

Thus, "oxicams" as defined herein are nonnarcotic analgesics/nonsteroidal antiinflammatory drugs which have the general formula:

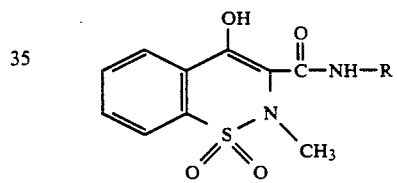

wherein R is an aryl or heteroaryl ring system.

The following NSAIDS may also be used: acemetacin, alminoprofen, amfenac sodium, aminoprofen, anitrazafen, antrafenine, auranofin, bendazac lysinate, benzydamine, beprozin, broperamole, bufezolac, carprofen, cinmetacin, ciproquazone, clidanac, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclofenac, fenclorac, fendosal, fenflumizole, fentiazac, feprazone, floctafenine, flunixin, flunoxaprofen, fluproquazone, fopirtoline, fosfosal, furcloprofen, furofenac, glucametacin, guaimesal, ibuproxam, isofezolac, isonixin, isoprofen, isoxepac, isoxicam, lefetamine HCl, leflunomide, lofemizole, lonazolac calcium, lotifazole, loxoprofen, lysin, clonixinate, meclofenamate sodium, meseclazone, microprofen, nabumetone, nictindole, nimesulide, orpanoxin, oxametacin, oxapadol, oxaprozin, perisoxal citrate, pimeprofen, pimetacin, piproxen, pirazolac, pirfenidone, pirprofen, pranoprofen, proglumetacin maleate, proquazone, pyridoxiprofen, sudoxicam, suprofen, talmetacin, talniflumate, tenoxicam, thiazolinobutazone, thielavin B, tiaprofenic acid, tiaramide HCl, tiflamizole, timegadine, tioxaprofen, tolfenamic acid, tolpadol, tryptamid, ufenamate, and zidometacin.

Finally, NSAIDS which may also be used include the salicylates, specifically aspirin, and the phenylbutazones, and pharmaceutically acceptable salts thereof.

Pharmaceutical compositions comprising the formula I or II and IIa compounds may also contain as the second active ingredient, antihistaminic agents such as benadryl, dramamine, histadyl, phenergan, and the like. Alternatively, they may include prostaglandin antagonists such as those disclosed in European Patent Application 11,067 or thromboxane antagonists such as those disclosed in U.S. Pat. No. 4,237,160. They may also contain histidine decarboxylase inhibitors such as α-fluoromethylhistidine, described in U.S. Pat. No. 4,325,961. The compounds of the formula I may also be advantageously combined with an $H_1$ or $H_2$-receptor antagonist, such as for instance cimetidine, ranitidine, terfenadine, famotidine, temelastine, acrivastine, loratadine, cetrizine, tazifylline, azelastine, aminothiadiazoles disclosed in EP 81102976.8 and like compounds, such as those disclosed in U.S. Pat. Nos. 4,283,408; 4,362,736; 4,394,508, and European Patent Application No. 40,696. The pharmaceutical compositions may also contain a $K^+/H^+$ ATPase inhibitor such as omeprazole, disclosed in U.S. Pat. 4,255,431, and the like. Each of the references referred to in this paragraph is hereby incorporated herein by reference.

The compound of the formula I and their salts may be prepared generally by the following processes.

The Scheme A provides a general method of preparation as follows:

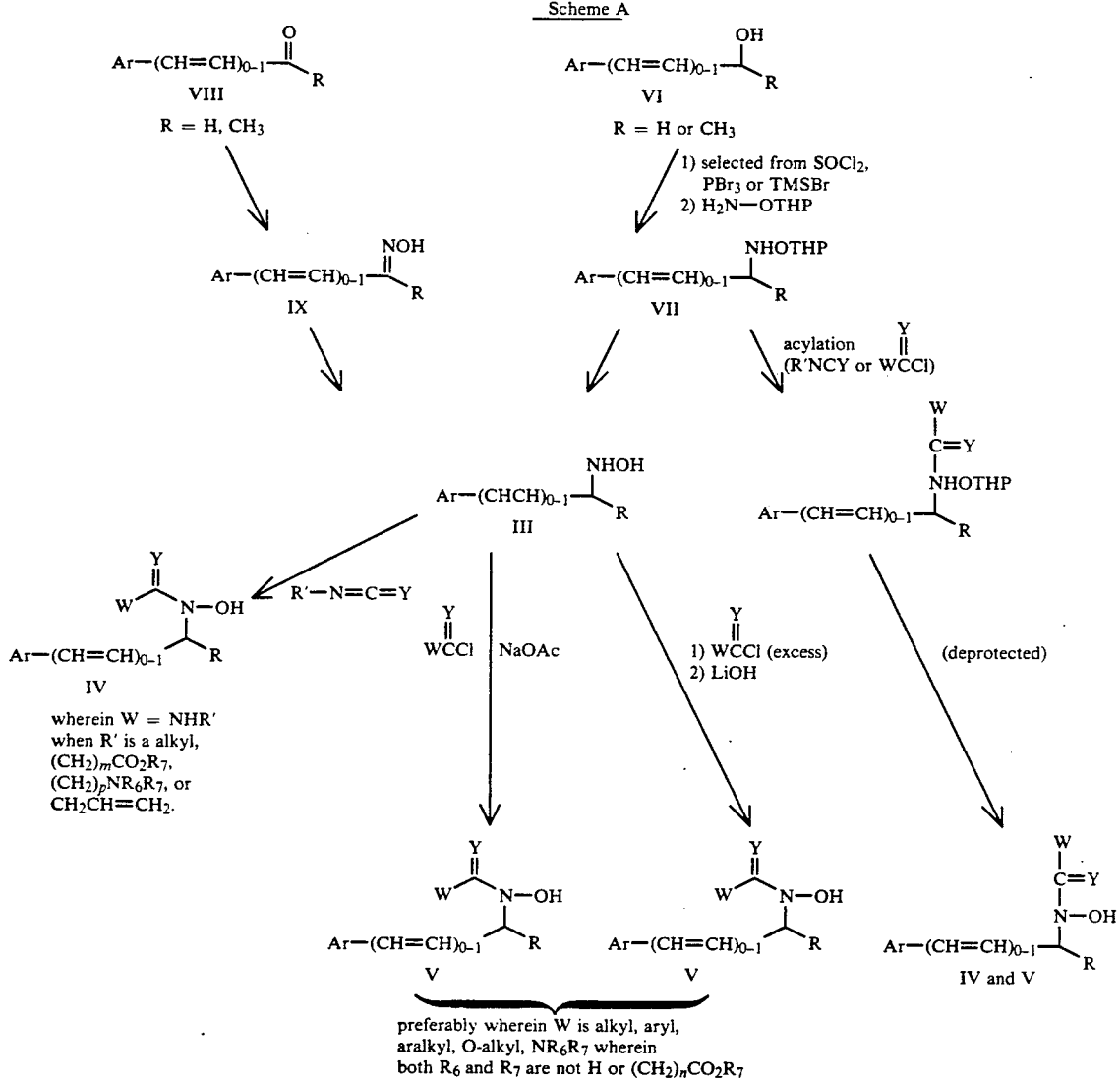

Generally, the reactions shown in Scheme A can be described as follows:

The oximes IX can be prepared from the aldehydes VIII(R=H) or ketones VIII(R=CH₃) by reacting with hydroxylamine.HCl in methanol or ethanol and sodium acetate at about −10° C. to reflux temperature for one hour to 48 hours depending on the nature of the carbonyl compound readily understood by an ordinarily skilled artisan. The oxime can also be prepared by reacting the carbonyl compound with NH₂OH.HCl in pyridine at about 20° C. to reflux temperature for 1.0 hour to 18 hours.

Reduction of the oxime IX is carried out with Na(CN)BH3 in acetic acid at about −5° C. to 40° C. for 1.0 hour to 18 hours. The Na(CN)BH3 reduction can also be carried out in methanol/HCl at about 0° C. to 35° C. for 2.0 hours to 24 hours. Borane pyridine complex in ethanol or methanol and dilute HCl can also be used for the reduction of oximes IX at about 10° C. to 40° C. for 2.0 hours to 24 hours.

The hydroxylamines III are acylated with an acid chloride, such as

and NaOAc in dioxane/water at about −5° C. to 30° C. for 30 minutes to 24 hours. Alternatively they can be acylated with an acid chloride such as

in CH$_2$Cl$_2$ in presence of an organic base such as triethylamine or diisopropylethylamine at about 10° C. to 35° C. but preferably at room temperature. In the latter case N-, O-diacylated product is formed which is hydrolyzed with aqueous inorganic base such as lithium hydroxide in an alcohol solvent at about 20° C to reflux temperature preferably at room temperature for 30 minutes to 8 hours to give the N-acylated product V.

The hydroxyureas IV(Y=O) and hydroxythioureas IV(Y=S) are prepared from the hydroxylamines III by reacting with the corresponding isocyanates or isothiocyanates in organic solvents such as toluene or toluene/THF mixture or toluene/DMF mixture at about 10° C. to about 40° C. for 2.0 hours to 24 hours, or in dioxane/water at about 0° C. to about 24° C. for two to 24 hours.

The hydroxylamines III can also be prepared by alkylation of O-protected hydroxylamine, followed by deprotection. That is, the alcohol VI is converted to its halo derivative. Then the halo derivative can be reacted with 1-5 equivalents of O-tetrahydropyranylhydroxylamine or O-trimethylsilylhydroxylamine in an organic solvent such as DMF or chloroform at about 20° C. to about 60° C. for one to 24 hours. Deprotection can be done under acidic conditions such as methanolic HCl at about 0° C. to reflux temperature for 15 minutes to 24 hours, or pyridinium p-toluenesulfonate in an alcohol solvent at about 0° C. to 60° C. for 15 minutes to three hours.

The intermediate 0-THP-hydroxylamines VII alternatively may be reacted with the acid chloride, i.e.

or isocyanate R'—N=C=O or isothiocyanate R'—N=C=S according to the method described above for the O-unprotected hydroxylamines with the acid catalyzed deprotection following acylation.

Scheme 1 below shows a novel method of preparing starting compounds wherein Ar is

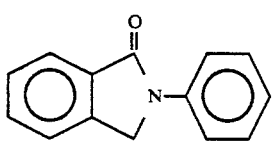

Scheme 1

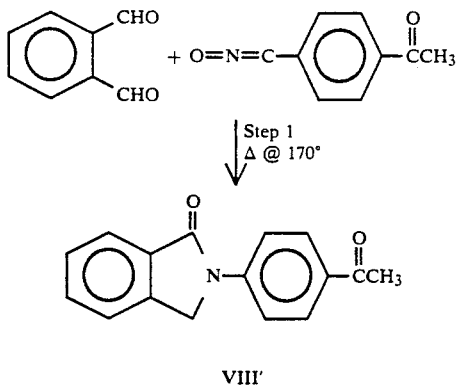

VIII'

In Scheme 1, N-Substituted phenyl-lH-isoindol-1-one VIII' is prepared by reacting oretho-phthalic dicarboxaldehyde with the corresponding substituted phenylisocyanate at an elevated temperature preferably at 170-180° C. without any solvent for 3 to 6 hours.

The acetophenone VIII' derivative is converted to the corresponding oxime by reacting with hydroxylamine HCl in pyridine at elevated temperature preferably at 100-110° C. for 2 to 8 hours. This latter conversion of the acetophenone VIII' to the oxime is as shown in Scheme A.

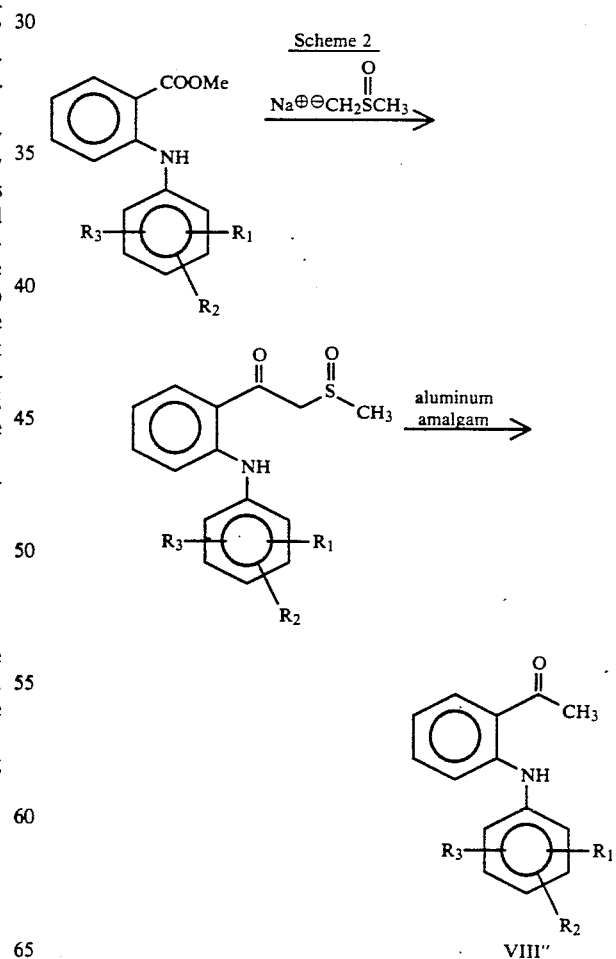

VIII"

The preferred process to prepare intermediate ketones VIII of Scheme A in the fenamate series is shown as VIII" in Scheme 2 above. Reaction of the ester with dimsyl anion

is followed by reduction of the intermediate β-ketosulfoxide with aluminum amalgam. Conditions are within the skill of an ordinary artisan. Conversion of the ketone to the compounds of formula I is as previously discussed for Scheme A.

example "Protective Groups in Organic Chemistry," J. F. W. McOmie, *Advances in Organic Chemistry*, Vol. 3, 191-281 (1963); R. A. Borssonas, *Advances in Organic Chemistry*, Vol. 3, 159-190 (1963); J. F. W. McOmie, *Chem. & Ind.*, 603 (1979), and T. W. Greene, "Protective Groups in Organic Synthesis", Wiley (New York) 1981, Chapters 2, 3, and 7.

Examples of suitable oxygen protecting groups are benzyl, t-butyldimethylsilyl, ethoxyethyl, methoxyethoxymethyl, and the like. Protection of an N—H containing moiety is necessary for some of the processes described herein for the preparation of compounds of

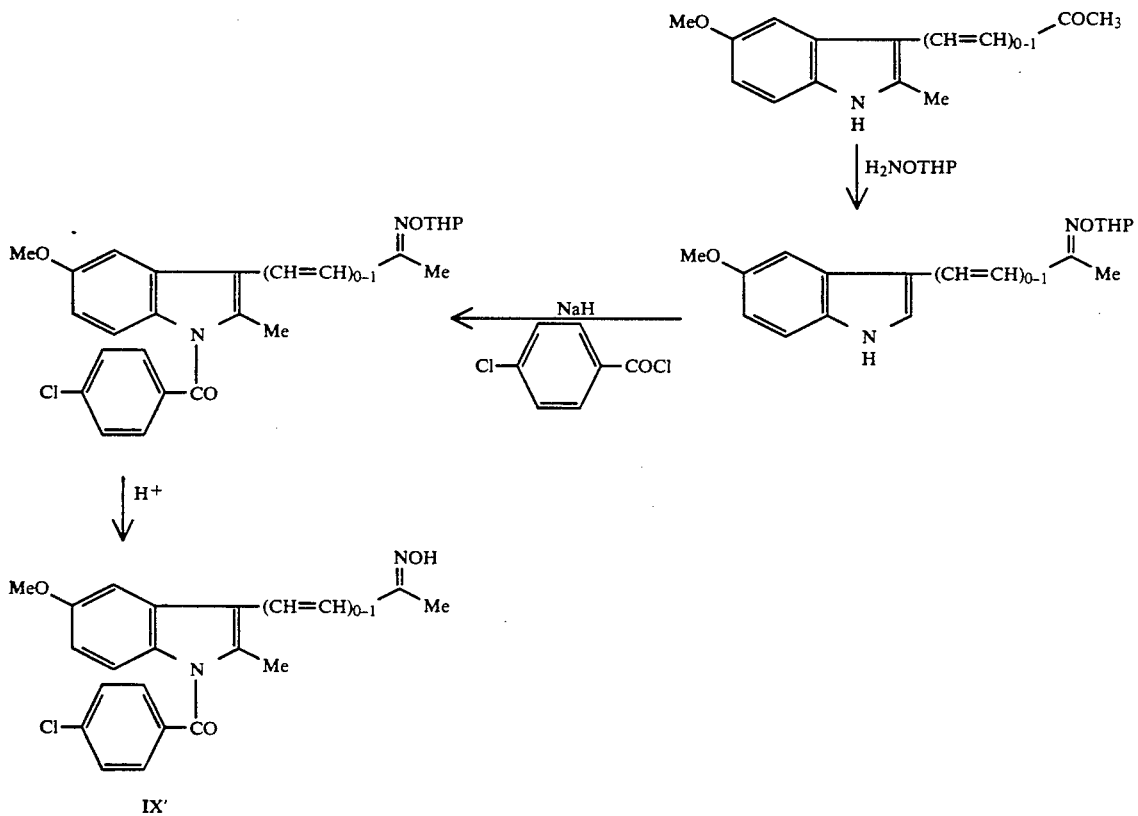

Scheme 3

The preferred method for preparing oximes IX of Scheme A in the indomethacin series IX' is shown in Scheme 3 above. Reaction of the methyl ketone with O-tetrahydropyranylhydroxylamine followed by acylation of the indole nitrogen with p-chlorobenzoyl chloride/sodium hydride and removal of the THP group with acid gives intermediate the oxime IX'. The oxime IX' is converted to compounds of formula I as previously discussed for Scheme A.

One of skill in the art would recognize variations in the sequence and would recognize appropriate reaction conditions from analogous reactions which may be appropriately used in the processes to make the compound of formula (I) herein. Further, the starting materials are known or can be prepared by known methods.

Under certain circumstances as discussed above, it is necessary to protect either the N or O of intermediates. The examples above showing this noted process with suitable protecting groups which are known are not meant to be limiting. Introduction and removal of such suitable oxygen and nitrogen protecting groups are well-known in the art of organic chemistry; see for this invention. Suitable nitrogen protecting groups are benzyl, triphenylmethyl, trialkylsilyl, trichloroethylcarbamate, trichloroethoxycarbonyl, vinyloxycarbamate acetyl, and the like.

Under certain circumstances it is necessary to protect two different oxygens with dissimilar protecting groups such that one can be selectively removed while leaving the other in place. The benzyl and t-butyldimethylsilyl groups are used in this way; either is removable in the presence of the other, benzyl being removed by catalytic hydrogenolysis, and t-butyldimethylsilyl being removed by reaction with, for example, tetra-n-butylammonium fluoride.

In the process described herein for the preparation of compounds of this invention the requirements for protective groups are generally well recognized by one skilled in the art of organic chemistry, and accordingly the use of appropriate protecting groups is necessarily implied by the processes of the charts herein, although not expressly illustrated.

17

The products of the reactions described herein are isolated by conventional means such as extraction, distillation, chromatography, and the like.

The invention is further elaborated by the representative examples as follows. Such examples are not meant to be limiting.

EXAMPLE 1

N-Hydroxy-9H-fluorene-2-methanamine

A solution of 2-fluorenecarboxaldehyde (26.23 g, 0.135 mol), hydroxylamine.HCl (31.2 g, 0.45 mol), and NaOAc (41.0 g, 0.50 mol) in methanol (250 mL) is stirred at 24° C. for 18 hours. The reaction mixture is filtered off from NaCl and the filtrate concentrated to dryness. The residue is extracted with $CH_2Cl_2$. The pooled extract is washed with water, dried ($Na_2SO_4$), and concentrated under reduced pressure to afford the oxime as a white solid. The crude oxime is recrystallized from n-hexane-$CH_2Cl_2$ to give analytically pure solid. Yield 21.2 g (75%); mp 158°-160° C. A solution of the oxime (4.2 g, 0.02 mol) in acetic acid (60 ml) is slowly treated with $Na(CN)BH_3$ (6.0 g, 0.096 mol) under nitrogen atmosphere. After the addition is complete the reaction mixture is stirred at 24° C. for 3.0 hours and then poured onto ice and NaOH solution to attain pH 14.0. The product is extracted with $CH_2Cl_2$. The organic layer is washed with water and brine, and then dried over Na Removal of solvent gives an oil which is allowed to crystallize from a small amount of $CH_2Cl_2$ to give white crystalline N-hydroxy-9H-fluorene-2-methanamine. Yield 2.6 g (61.5%); mp 150°-152° C.

Anal. Calcd for $C_{14}H_{13}NO$:
C, 79.59; H, 6.20; N, 6.63.
Found: C, 79.35; H, 6.15; N, 6.57.

EXAMPLE 2

(9H-Fluoren-2-ylmethyl)hydroxyamino-oxo-acetic acid, ethyl ester

The crude hydroxylamine (4.2 g, 0.02 mol) from Example 1 is dissolved in dioxane (80 ml) and water (50 ml). The turbid solution is cooled to −5° C. and then treated with NaOAc (3.3 g, 0.04 mol) followed by ethyl oxalylchloride (3.0 g, 0.022 mol). The mixture is stirred at 24° C. for 3.0 hours, poured onto ice-1N HCl (40 mL) and extracted with $CH_2Cl_2$. The extract is washed with brine, water and dried over Na The solvent is distilled off to give (9H-fluoren-2-ylmethyl)hydroxyamino-oxo-acetic acid, ethyl ester which is fractionally recrystallized from isopropyl ether and $CH_2Cl_2$ and then from isopropyl ether. Yield 1.6 g (26%); mp 130°-131° C.

Anal Calcd for $C_{18}H_{17}NO_4$:
C, 69.44; H, 5.50; N, 4.50
Found: C, 69.72; H, 5.53; N, 4.39

EXAMPLE 3

(9H-Fluoren-2-ylmethyl)hydroxyamino-oxo-acetic acid

The crude ester (1.9 g, 6 mmol) from Example 2 is dissolved in ethanol (30 ml) and water (30 ml) and then treated with 1N NaOH solution (12.2 ml, 12 mmol). The mixture is stirred at room temperature for 15 minutes and then warmed on a steam bath for five minutes. The cooled solution is diluted with water (300 ml), filtered and then acidified with 1N HCl to pH 1.0 when (9H-fluoren-2-ylmethyl) hydroxyamino-oxo-acetic acid precipitated out. The crude product is triturated with methanol and $CH_2Cl_2$ to give the analytical product. Yield 0.42 g (22%); mp>260° C.

Anal. Calcd for $C_{16}H_{13}NO_4.2H_2O$:
C, 60.18; H, 5.37; N, 4.39
Found: C, 60.54; H, 3.91; N, 4.31

EXAMPLE 4

N-(9H-Fluoren-2-ylmethyl)-N-hydroxy-acetamide

The crude hydroxylamine (4.2 g, 0.02 mol) from Example 1 is dissolved in dioxane (100 ml) and water (50 ml) and cooled to −5° C. The cooled solution is treated with sodium acetate (3.3 g, 0.04 mol) and acetyl chloride (1.75 g, 0.022 mol) and the resulting mixture is stirred at 24° C. for 30 minutes and poured onto ice and dilute HCl when N-(9H-fluoren-2-ylmethyl)-N-hydroxy-acetamide precipitated out. The crude product is filtered, washed and dried and then recrystallized from THF and isopropyl ether. Yield 3.3 g (65%); mp 182°-183° C.

Anal. Calcd for $C_{16}H_{15}NO_2$:
C, 75.87; H, 5.97; N, 5.53.
Found: C, 75.79; H, 5.76; N, 5.60.

EXAMPLE 5

N-(9H-Fluoren-2-ylmethyl)-N-hydroxy-2-methyl-propanamide

Using the method in Example 4, N-hydroxy-9H-fluroene-2-methanamine is reacted with isobutyryl chloride to give N-(9H-fluoren-2-ylmethyl)-N-hydroxy-2-methyl-propanamide as white crystalline solid. Yield 3.5 g (62%); mp 163°-166° C.

Anal. Calcd for $C_{18}H_{19}NO_2$:
C, 76.84; 6, 6.81; N, 4.98.
Found: C, 76.41; H, 6.72; N, 4.88, 4.89.

EXAMPLE 6

N-(9H-Fluoren-2-ylmethyl)-N-hydroxy-N'-methylurea

N-Hydroxy-9H-fluorene-2-methanamine (2.16 g, 0.01 mol) from Example 1 is dissolved in a mixture of toluene (120 ml) and DMF (20 ml) and then treated with methyl isocyanate. The solution is stirred at room temperature for 18 hours when N-(9H-fluoren-2-ylmethyl)-N-hydroxy-N'-methylurea slowly crystallized out. It is filtered, washed with toluene and dried in vacuo at 65° C. Yield 1.83 g (68%); mp 196°-198° C. (dec).

Anal. Calcd for $C_{16}H_{16}N_2O_2$:
C, 71.62; H, 6.01; N, 10.44.
Found: C, 71.39; H, 5.92; N, 10.19.

EXAMPLE 7

30 N-Hydroxy-c-methyl-9H-fluorene-2-methanamine

2-Acetylfluorene oxime (11.34 g, 0.05 mol) (prepared according to the method described in *J. Med. Chem.*, 1988, 31, 60) is suspended in acetic acid (75 ml) and is then treated with $Na(CN)BH_3$ (15.0 g, 0.25 mol) slowly over 10 minutes when a clear solution is formed. The reaction mixture is poured onto ice (500 g), water (300 ml), and 50% NaOH solution (85 g) and the pH is adjusted to 7.0 with $NaHCO_3$ solution. The product is extracted with $CH_2Cl_2$, washed with water, dried over $Na_2SO_4$ and evaporated to dryness to give a semisolid residue (16 g). Trituration with $CH_2Cl_2$-isopropylether gives the pure N-hydroxy-o-methyl-9H-fluorene-2-methanamine. Yield 2.34 g (21%); mp 144°-147° C. The filtrate is evaporated to give more crude product which is used in the next step without any further purification.

Anal. Calcd for $C_{15}H_{15}NO$:
C, 79.97; H, 6.71; N, 6.22.
Found: C, 80.25; H, 6.72; N, 6.21.

EXAMPLE 8

N-(1-(9H-Fluoren-2-yl)ethyl)-N-hydroxy-N'-methylurea

The crude hydroxylamine (3.89 g, 0.017 mol) from Example 7 is dissolved in toluene (50 ml) and then treated with methyl isocyanate (0.99 g, 0.017 mol). The solution is stirred at 24° C. for 72 hours when the product slowly crystallized out. It is filtered, washed with toluene, and then washed thoroughly with $CH_3OH$, $CH_2Cl_2$ and isopropyl ether mixture (5:10:30). The $CH_3OH$, $CH_2Cl_2$ and isopropyl ether mixture (5:10:30) wash is allowed to stand at 24° C. overnight when the analytically pure N-(1-(9H-fluoren-2-yl)ethyl)-N-hydroxy-N'-methylurea slowly crystallized out. It is dried in vacuo at 78° C. Yield 0.43 g (9.0%); mp 175°–178° C. (dec).

Anal Calcd for $C_{17}H_{18}N_2O_2$:
C, 72.32; H, 6.43; N, 9.92.
Found: C, 72.12; H, 6.46; N, 10.03.

EXAMPLE 9

N'-Ethyl-N-(1-(9H-fluoren-2-yl)ethyl)-N-hydroxyurea

The hydroxylamine from Example 7 is reacted with ethyl isocyanate according to the method described in Example 8 to give N'-ethyl-N-(1-(9H-fluoren-2-yl)ethyl)-N-hydroxyurea. Yield 1.4 g (33%); mp 128°–132° C. (dec). Anal. Calcd for C .0.75 $H_2O$:
C, 69.76; H, 6.99; N, 9.04
Found: C, 69.42; H, 6.52; N, 8.96

EXAMPLE 10

N-(1-(9H-Fluoren-2-Yl)ethyl)-N-hydroxy-N'-methylthiourea

The hydroxylamine from Example 7 is reacted with methyl isothioicyanate according to the method described in Example 8 to give the N-(1-(9H-fluoren-yl)ethyl)-N-hydroxy-N'-methylthiourea. Yield 2.0 g (94.4%); mp 171°–172° C. (dec).

Anal. Calcd for $C_{17}H_{18}N_2OS$:
C, 68.44; H, 6.08; N, 9.39; S, 10.73.
Found: C, 68.48; H, 5.75; N, 9.15; S, 11.05.

EXAMPLE 11

N-(1-(9H-Fluoren-2-yl)ethyl)-N-hydroxy-acetamide

The crude hydroxylamine (4.5 g, 0.02 mol) from Example 7 is dissolved in dioxane (50 ml) and water (50 ml) and the solution is cooled to 5° C. The solution is then treated with NaOAc (3.3 g, 0.04 mol) and acetyl chloride (1.73 g, 0.022 mol) and the mixture stirred at 24° C. for 2.0 hours. It is poured onto ice, $H_2O$, and 1N HCl (pH 1.0) when the product oiled out. The product is taken up in $CH_2Cl_2$, washed with water and dried (Na The solvent is evaporated off to give an oil which on trituration with isopropyl ether gives a solid which is recrystallized from isopropyl ether to give N-(1-(9H-fluoren-2-yl)ethyl)-N-hydroxy-acetamide. Yield 1.0 g (18%); mp 168°–171° C.

Anal Calcd for $C_{17}H_{17}NO_2.0.20\ H_2O$:
C, 75.37; H, 6.47; N, 5.17.
Found: C, 75.67, 75.38; H, 6.24, 6.67; N, 5.22, 5.53.

EXAMPLE 12

N-Hydroxy-alpha-methyl-9H-fluorene-2-methanamine carbamic acid, ethyl ester The crude hydroxylamine (10.0 g, 0.044 mol) from Example 7 is reacted with ethyl chloroformate according to the method described in Example 11 to give the title compound which is purified by flash chromatography through silica gel to give analytical N-Hydroxy-alpha-methyl-9H-fluorene-2-methanamine carbamic acid, ethyl ester. Yield 1.4 g (11%); mp 111°–112° C.

Anal. Calcd for $C_{18}H_{19}NO_3.0.10\ H_2O$:
C, 72.27; H, 6.47; N, 4.68.
Found: C, 72.09; H, 6.15; N, 4.28.

EXAMPLE 13

N-(1-(9H-Fluoren-2-yl)-N-hydroxy-2-methyl-propanamide

The crude hydroxylamine (8.4 g, 0.037 mol) from Example 7 is reacted with isobutyryl chloride according to the method described in Example 11 to give the title compound which is purified by flash chromatography through silica gel to give analytical N-(1-(9H-fluoren-2-yl)-N-hydroxy-2-methylpropanamide. Yield 0.5 g (4.6%); mp 184°–186° C. (dec).

Anal. Calcd for $C_{19}H_{21}NO_2$:
C, 77.26; H, 7.17; N, 4.74.
Found: C, 76.79; H, 6.95; N, 4.49.

EXAMPLE 14

N-(1-(9H-Fluoren-2-yl)ethyl)-N-hydroxy-N'-ethylthiourea

The crude hydroxylamine from Example 7 is reacted with ethyl isothiocyanate according to the method described in Example 8 to give N-(1-(9H-fluoren-2-yl)ethyl)-N-hydroxy-N'-ethylthiourea. Yield 100 mg (80%); mp 158°–159° C. (dec).

Anal Calcd for $C_{18}H_{20}N_2OS$:
C, 69.20; H, 6.45; N, 8.97; S, 10.26.
Found: C, 69.20; H, 6.72; N, 8.96; S, 9.81.

EXAMPLE 15

6,11-Dihydro-11-oxobibenz[b,e]oxepin-3-carboxaldehyde, oxime

A mixture of 6,11-dihydro-11-oxodibenz[b,e]oxepin-3-carboxaldehyde in Toshiyuki Yoshioka et al, *J. Med. Chem.*, (1978), 21, 633 (14.95 g, 0.06 mol), hydroxylamine hydrochloride (8.7 g, 0.120 mol), sodium acetate (10.25 g, 0.12 mol) in tetrahydrofuran (300 ml) and methanol (50 ml) is stirred at room temperature for 16 hours. After removal of the solvent under reduced pressure, the residue is dissolved in ethyl acetate. The organic layer is separated, washed with water, dried and the solvent is removed to give 15.9 g of a solid mp 170°–172° C. Recrystallization from methanol gives 11.63 g (73%) of 6,11-dihydro-11-oxodibenz[b,e]oxepin-3-carboxaldehyde oxime, mp 170°–172° C.

C,H,N analysis Calcd for $C_{15}H_{11}NO_3$:
C, 71.14; H, 4.37; N, 5.53.
Found: C, 71.10; H, 4.06; N, 5.41.

EXAMPLE 16

3[(Hydroxyamino)methyl]dibenz[b,e]oxepin-11(6H)-one

Sodium cyanoborohydride (13.6 g, 0.22 mol) is added in portions to a solution of 6,11-dihydro-11-oxodibenz[b,e]oxepin-3-carboxaldehyde, oxime (11 g; 0.04 mol) in acetic acid (150 ml) at 15-20° C. (cooling). After the mixture is stirred for 2.5 hours, an additional portion of sodium cyanoborohydride (2 g) is added and the solution is stirred for an additional 2 and ¾ hours. The mixture is neutralized to pH ~7 with 50% sodium hydroxide solution, the temperature being maintained at 65° C. The product is extracted with ethyl acetate, followed by washings with water, saturated sodium chloride solution, drying and evaporating under reduced pressure to give 13.2 g of a solid residue. The residue is flash chromatographed on silica gel with chloroform then with chloroform:methanol=95:5, as eluant to give 8.66 g (78%); 3[(hydroxyamino)methyl]dibenz[b,el]oxepin(-11(6H)-one, as a solid.

EXAMPLE 17

N[(6,11-Dihydro-11-oxodibenz[b,el]oxepin-3-yl)methyl]N-hydroxy-2-methylpropanamide To a solution of 3[(hydroxyamino) methyl]dibenz[b,e]oxepin-11(6H)-one (5.5 g, 0.02 mol) sodium acetate (5.8 g, 0.04 mol) in dioxane (120 ml) and water (60 ml) isobuturyl chloride (2.55 g, 0.023 mol) is added. After the mixture is stirred for one hour at room temperature, lithium hydroxide (1 g) is added and the solution is stirred for 18 hours. The mixture is acidified with 1N hydrochloric acid, poured into ice water and extracted with ethyl acetate. The organic layer is washed successively with water, sodium bicarbonate solution and water, dried over sodium sulfate and evaporated to give 7.1 g of oily residue. Flash chromatography on silica gel with methylene chloride:methanol=95:5 as eluant, gives 5.3 g of the product. Further purification is accomplished by flash chromatography on silica gel with methylene chloride:ethyl acetate=80:20 as eluant giving 3.4 g of a solid, which on recrystallization from methylene chloride-hexane, yielded 2.6 g (37%) of analytically pure N-[6,11-dihydro-11-oxodibenz[b,el]oxepin-3-yl]methyl]-N-hydroxy-2-methylpropanamide, mp 128-131° C.

C,H,N analysis Calcd for $C_{19}H_{19}NO_4$:
C, 70.16; H, 5.89; N, 4.31.
Found: C, 70.25; H, 5.88; N, 4.21.

EXAMPLE 18

N-[(6,11-Dihydro-11-oxodibenz[b,el]oxepin-3-yl)methyl]-N-hydroxyacetamide

Sodium cyanoborohydride (3 g, 0.047 mol) is added in portions to a suspension of 6,11-dihydro-11-oxodibenz[b,el]oxepin-3-carboxaldehyde, oxime (4 g, 0.016 mol) in acetic acid (70 ml) at ca 15° C. (cooling). After the mixture is stirred for four hours at room temperature, acetic anhydride (1.8 g) is added. The solution is stirred at room temperature for 3 and ¼ hours, poured into ice water and extracted with ethyl acetate. The organic layer is separated and washed successively with 1N hydrochloric acid, water, sodium bicarbonate solution and water, then dried and evaporated to give 3.9 g of a residue. The residue was treated with lithium hydroxide (1.8 g), methanol (30 ml), water (10 ml), then stirred for one hour. The mixture is then poured into water, acidified and the product is isolated with ethyl acetate to give 3.2 g of oily residue. Flash chromatography on silica gel with methylene chloride:ethyl acetate=8:2, then with ethyl acetate as eluant yields 2.6 g of a residue. Repeat flash rechromatography on silica gel with chloroform:methanol=9:1 as eluant gives 2.2 g (47%) N-[(6,11-dihydro-11-oxodibenz[b,e]oxepin-3-yl]methyl]-N-hydroxyacetamide, as a solid, mp 65-115° C.

C,H,N analysis Calcd for $C_{17}H_{15}NO_4$:
C, 68.67; H, 5.08; N, 4.71.
Found: C, 68.14; H, 5.14, N, 4.48.

EXAMPLE 19

Ethyl[[(6,11-Dihydro-11-oxodibenz[b,e]oxepin-3-yl)methyl]hydroxyamino]oxoacetate To a solution of 3[(hydroxyamino) methyl]dibenz[b,e]oxepin-11(6H)-one (4.25 g, 0.016 mol), sodium acetate (4.5 g, 0.03 mol) in dioxane (90 ml) and water (40 ml) at 5°-10° C. is added ethyl oxalylchloride (2.27 g, 0.016 mol). The mixture is stirred at 5°-10° C. for 30 minutes, then at room temperature for three hours, poured into ice water and extracted with ethyl acetate. The ethyl acetate layer is washed successively with water, sodium bicarbonate solution and water, then dried and evaporated to give 5.2 g of oily residue. Flash chromatography on silica gel, then rechromatography with methylene chloride:methanol=95:5, as eluant gives 1.6 g (27%) of ethyl [[(6,11-dihydro-11-oxodibenz[b,e]oxepin-3-yl)methyl]hydroxyamino]oxoacetate, as a solid, mp 52°-62° C.

C,H,N analysis Calcd for $C_{19}H_{17}NO_6$:
C, 64.22; H, 4.82; N, 3.90.
Found: C, 63.91; H, 4.79; N 3.66.

EXAMPLE 20

N-[(6,11-Dihydro-11-oxodibenz[b,e]oxepin-3-yl) methyl]-N-hydroxy-N'-methylurea Methylisocyanate (0.89 g, 0.016 mol) in toluene (10 ml) is added dropwise to a solution of 3[(hydroxyamino)methyl]dibenz[b,el]oxepin-11(6H)-one (4 g, 0.016 mol) in toluene (50 ml) and tetrahydrofuran (50 ml). The mixture is stirred for 18 hours at room temperature to give 2.48 g (51%) of the desired product, mp 155°-157° C. Recrystallization from methanol-ethylacetate gives 1.75 g (36%) of N[(6,11-dihydro-11-oxodibenz[b,el]oxepin-3-yl)methyl]-N-hydroxy-N'-methylurea, as a white crystalline solid, mp 156°-158° C.

C,H,N analysis Calcd for $C_{17}H_{16}N_2O_4$:
C, 65.37; H, 5.16; N, 8.97.
Found: C, 65.29; H, 5.17; N, 8.93.

EXAMPLE 21

4-(1,3-Dihydro-1-oxo-2H-isoindol-2-yl)benzoic acid, ethyl ester

A mixture of o-phthalicdicarboxaldehyde (17.54 g, 0.131 mol) and p-carbethoxyphenylisocyanate (25.0 g, 0.131 mol) is heated in an oil bath at 170° C. for 4.0 hours under nitrogen atmosphere. The hot melt is then slowly poured into CHC13 (300 ml). The solution is then evaporated to dryness when a solid residue is obtained. The crude 4-(1,3-dihydro-1-oxo-2H-isoindol-2-yl)benzoic acid, ethyl ester is triturated with isopropyl ether and then recrystallized from $CH_2Cl_2$ - isopropyl ether (1:1, 300 ml) to give white solid. Yield 5.07 g (13.8%); mp 182°-184° C.

Anal. Calcd for $C_{17}H_{15}NO_3$:
C, 72.58; H, 5.37; N, 4.98.
Found: C, 72.52; H, 5.41; N, 4.81.

EXAMPLE 22

4-(1,3-Dihydro-1-oxo-2H-isoindol-2-yl)benzoic acid

A mixture of 4-(1,3-dihydro-1-oxo-2H-isoindol-2-yl)benzoic acid, ethyl ester (2.55 g, 0.009 mol), 1N NaOH (20 ml), water (70 ml), and methanol (70 ml) is heated to reflux for 20 minutes when a clear solution is formed. The reaction mixture is filtered and the filtrate is carefully acidified with 4N HCl (6 ml) to pH 1.0 when a solid pptd. out. The crude 4-(1,3-Dihydro-1-oxo-2H-isoindol-2-yl)benzoic acid is filtered, washed with hot CH3OH and dried to give analytical sample. Yield 1.67 g (73%); mp >295° C.

Anal. Calcd for $C_{15}H_{11}NO_3$:
C, 71.14; H, 4.37; N, 5.53.
Found: C, 71.03; H, 4.37; N, 5.47.

Examples 21 and 22 are useful as representative preparations of intermediates for the preparation of aldehydes shown as I in Scheme A.

EXAMPLE 23

2-(4-Acetylphenyl)-2,3-dihydro-1H-isoindole-1-one

A mixture of 4-acetylphenylisocyanate (27.5 g, 0.17 mol) and o-phthalicdicarboxaldehyde (25.0 g, 0.186 mol) is heated in an oil bath at 170°-175° C. for 4.0 hours under nitrogen atmosphere. On cooling the melt solidified which is pulverized and refluxed with $CH_2Cl_2$ and CH3OH and filtered to give 18.2 g (41.4%) of the desired 2-(4-acetylphenyl)-2,3-dihydro-1H-isoindole-1-one, mp 235°-237° C. The residue is recrystallized from DMF (1800 ml). Yield 13.0 g (29.6%), mp 236°-239° C. (Jap. patent J5 7050-960; mp 243°-244° C. for the nonsolvated compound, prepared by a different route).

Anal. Calcd for $C_{16}H_{13}NO_2 \cdot 0.10$ DMF:
C, 75.70; H, 5.34; N, 5.96
Found: C, 75.35; H, 5.15; N, 5.51.

EXAMPLE 24

2,3-Dihydro-2-(4-(1-hydroxyimino)ethyl)phenyl)-1H-isoindole-1-one

A mixture of 2-(4-acetylphenyl)-2,3-dihydro-1H-isoindole-1-one (2.6 g, 0.01 mol), hydroxylamine.HCl (2.1 g, 0.03 mol) and pyridine (25 ml) is heated at 100° C. for 4.0 hours when a clear solution is formed. It is allowed to cool to 24° C. when 2,3-dihydro-2-(4-(1-hydroxyimino)ethyl)phenyl)-1H-isoindole-1-one crystallized out. Yield 2.65 g (100%); mp 265°-269° C (dec).

Anal. Calcd for $C_{16}H_{14}N_2O_2$:
C, 72.16; H, 5.30; N, 10.52.
Found: C, 71.36, 71.93; H, 5.28, 5.51; N, 10.34, 10.64.

EXAMPLE 25

2-[(2,6-Dichlorophenyl)amino]benzoic acid, methyl ester

To a solution of 2-[(2,6-dichlorophenyl) amino]benzoic acid (25 g, 89 mmol) [J. S. Kaltenbronn et al, *Arzneim-Forsch/Drug Res.* 33(1),4a, 621-627 (1983)] and dimethylformamide (6.8 g, 93 mmol) in dry tetrahydrofuran (500 ml) is added oxalyl chloride (17 ml, 196 mmol) dropwise with stirring under an atmosphere of dry nitrogen at 0° C. The ice bath is removed and the reaction mixture is stirred without cooling for 15 minutes. The reaction mixture is poured into methanol (1500 ml). The solvent is evaporated and the residue is partitioned between ethyl acetate and saturated aqueous sodium bicarbonate. The organic layer is dried (MgSO4) and evaporated. Recrystallization of the residue from methanol provides pure 2-[(2,6-dichlorophenyl) amino]benzoic acid, methyl ester (21.9 g, 83%); mp 100°-103° C.

Anal. Calcd for $C_{14}H_{11}Cl_2NO_2$:
C, 56.78; H, 3.74; N, 4.73.
Found: C, 56.71; H, 3.73; N, 4.79.
Cl Calcd 23.94.
Found: 23.17.

EXAMPLE 26

2-[(2,3-Dimethylphenyl)amino]benzoic acid, methyl ester

A suspension of 2-[(2,3-dimethylphenyl) amino]benzoic acid (mefenamic acid) 35 g, 145 mmol) in methanol (600 ml) and concentrated sulfuric acid (15 ml) is heated at reflux for two days. The reaction mixture is cooled in an ice bath. The resulting solid is collected by filtration and recrystallized from methanol to give 2-[(2,3-dimethylphenyl)amino]benzoic acid, methyl ester (32.0 g, 86%); mp 98°-100° C.

Anal Calcd for $C_{16}H_{17}NO_2$:
C, 75.27; H, 6.71; N, 5.49.
Found: C, 75.29; H, 6.75; N, 5.46.

EXAMPLE 27

2-[(2,6-Dichloro-3-methylphenyl)amino]benzoic acid, methyl ester

2-[(2,6-Dichloro-3-methylphenyl)amino]benzoic acid is reacted with oxalyl chloride and methanol according to the procedure of Example 25 to give 2-[(2,6-dichloro-3-methylphenyl)amino]benzoic acid, methyl ester in 89% yield; mp 132°-134° C.

EXAMPLE 28

2-[[3-(Trifluoromethyl)phenyl]amino]benzoic acid, methyl ester

Reaction of 2-[[3-(trifluoromethyl)phenyl]amino]benzoic acid with methanol and sulfuric acid according to the procedure of Example 26 gives a 71% yield of 2-[[3-(trifluoromethyl)phenyl]amino]benzoic acid, methyl ester as a colorless oil.

EXAMPLE 29

2-[(2,3-Dimethylphenyl)amino]benzyl alcohol

A solution of 2-[(2,3-dimethylphenyl) amino]benzoic acid, methyl ester (31 g, 121.5 mmol) in dry ether (600 ml) is added dropwise to a suspension of lithium aluminum hydride (6.9 g, 0.18 mmol) in dry ether (200 ml) under an atmosphere of dry nitrogen. The reaction mixture is stirred at room temperature overnight and quenched by the careful dropwise addition of water (7 ml), 15% NaOH (7 ml) and water (20 ml). The resulting suspension is filtered and the filtrate is evaporated to an oil which crystallizes upon addition of hexane to give pure 2-[(2,3-dimethylphenyl)amino]benzyl alcohol (26 g, 94%); mp 65°-69° C.

Anal. Calcd for $C_{15}H_{17}NO$:
C, 79.26; H, 7.54; N, 6.16.
Found: C, 79.20; H, 7.54; N, 6.05.

The following compounds are prepared according to the procedure of Example 29:

[Structure: benzene ring with CH2OH and NH-Q substituents ortho]

| Example No. | Q | mp °C. | % Yield | Prepared from the Compound of the Example |
|---|---|---|---|---|
| 30 | [2,6-dichlorophenyl] | 109-112 | 97% | Ex. 25 |
| 31 | [2,3-dichloro-4-methylphenyl] | 145-146 | 75% | Ex. 27 |
| 32 | [3-trifluoromethylphenyl] | oil | 89% | Ex. 28 |

EXAMPLE 33

2-[(2,3-Dimethylphenyl)amino]-benzaldehyde

A suspension of pyridinium chlorochromate (47.5 g, 0.22 mol) and neutral alumina (170 g) in dichloromethane (600 ml) is stirred for 30 minutes at room temperature. 2-[(2,3-dimethylphenyl) amino]benzyl alcohol (25 g, 0.11 mol) is added and the reaction mixture is stirred at room temperature overnight. The suspension is filtered through a pad of silica gel (1000 g) and the product is eluted with dichloromethane (2500 ml). The combined filtrate and eluant are evaporated and the residue is recrystallized from cold methanol/water to give 2-[(2,3-dimethylphenyl)amino] benzaldehyde (11.95 g, 48%). Recrystallization from hexane at 0° C. gives analytical material; mp 45-47° C.

Anal. Calcd for $C_{15}H_{15}NO$.

C, 79.97; H, 6.71; N, 6.22.

Found: C, 79.84; H, 6.75; N, 6.38.

The following compounds are prepared according to the procedure of Example 33:

[Structure: benzene ring with CHO and NH-Q substituents ortho]

| Example No. | Q | mp °C. | % Yield | Prepared from the Compound of the Example |
|---|---|---|---|---|
| 34 | [2,6-dichlorophenyl] | 108-112 | 76% | Ex. 30 |

Anal. Calcd for $C_{13}H_9Cl_2NO$:

| | C, 58.67; | H, 3.41; | N, 5.26; | Cl, 26.64 |
|---|---|---|---|---|
| Found: | C, 58.73; | H, 3.38; | N, 5.10; | Cl, 26.78 |

| 35 | [2,3-dichloro-4-methylphenyl] | 90-91 | 73% | Ex. 31 |

Anal. Calcd. for $C_{14}H_{11}Cl_2NO$:

| | C, 60.02; | H, 3.97; | N, 5.00; | Cl, 25.31 |
|---|---|---|---|---|
| Found: | C, 60.15; | H, 3.96; | N, 4.98; | Cl, 25.42 |

| 36 | [3-trifluoromethylphenyl] | 54-56 | 64% | Ex. 32 |

Anal. Calcd. for $C_{14}H_{10}F_3NO$:

| | C, 63.39; | H, 3.81; | N, 5.28; | Cl, 21.49 |
|---|---|---|---|---|
| Found: | C, 63.56; | H, 3.81; | N, 5.23; | Cl, 21.03 |

EXAMPLE 37

2-[(2,3-Dimethylphenyl)amino]benzaldehyde oxide

A solution of 2-[(2,3-dimethylphenyl)amino]benzaldehyde (11 g, 0.049 mol) and hydroxylamine hydrochloride (17 g, 0.25 mol) in pyridine (250 ml) is stirred at room temperature overnight. The solvent is evaporated and the residue is partitioned between ethyl acetate (200 ml) and 10% aqueous HCl (200 ml). The organic layer is washed with 10% aqueous HCl (200 ml) and water (2×100 ml). The organic layer is dried (MgSO4) and the solvent is evaporated to give 2-[(2,3-dimethylphenyl) amino]benzaldehyde oxime which is recrystallized from hexane. Yield 7.3 g (62%); mp 107°-108° C.

Anal. Calcd for $C_{15}H_{16}N_2O$:

C, 74.97; H, 6.71; N, 11.66.

Found: C, 75.32; H, 6.69; N, 11.34.

The following compounds are prepared according to the procedure of Example 37:

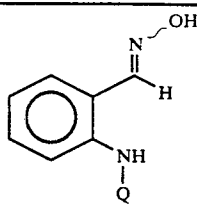

| Example No. | Q | mp °C. | % Yield | Prepared from the Compound of the Example |
|---|---|---|---|---|
| 38 | 2,6-dichlorophenyl | 82–85 | 78% | Ex. 34 |

Anal. Calcd for $C_{13}H_{10}Cl_2N_2O$:
C, 55.54; H, 3.59; N, 9.96; Cl, 25.22
Found: C, 55.38; H, 3.53; N, 9.92; Cl, 25.36

| 39 | 2,6-dichloro-3-methylphenyl | oil | 78% | Ex. 35 |

Anal. Calcd for $C_{14}H_{12}Cl_2N_2O \cdot 0.13H_2O$:
C, 56.51; H, 4.16; N, 9.42; Cl, 23.83; $H_2O$, 0.79
Found: C, 56.16; H, 4.44; N, 9.09; Cl, 23.08; $H_2O$, 0.44

| 40 | 3-trifluoromethylphenyl | oil | 91% | Ex. 36 |

EXAMPLE 41

2-[(2,3-Dimethylphenyl)amino]-N-hydroxybenzenemethanamine

To a solution of 2-[(2,3-dimethylphenyl)amino]benzaldehyde oxime (2.0 g, 8.4 mmol) and methyl orange (20 mg as an indicator), in methanol (40 ml) and water (10 ml) is added sodium cyanoborohydride (4.0 g, 64 mmol) in small portions over two hours, maintaining a red color of the indicator by the dropwise addition of concentrated HCl. The reaction of mixture is diluted with ethyl acetate (200 ml) and the aqueous layer is neutralized to pH=7 with 1N NaOH. The organic layer is collected, dried (MgSO ) and the solvent is evaporated to give crude 2-[(2,3-dimethylphenyl)amino]-N-hydroxy-benzenemethanamine as an oil which is used without further purification in the next step.

EXAMPLE 42

2-[(2,6-Dichlorophenyl)amino]-N-hydroxybenzenemethanamine

To a solution of 2-[(2,6-dichlorophenyl)amino]benzaldehyde oxime (4.0 g, 13.6 mmol) in glacial acetic acid (20 ml) is added sodium cyanoborohydride (2.05 g, 33 mmol) in small portions over a period of two hours. The reaction mixture is diluted with ethyl acetate (200 ml) and neutralized with 1N NaOH. The organic layer is collected and the solvent is evaporated. 2-[(2,6-Dichlorophenyl)amino]-N-hydroxybenzenemethanamine (3.5 g, 91%) is isolated as an oil by flash chromatography (silica, 3:1 chloroformethyl acetate). The compound is not further purified, but used directly in the next reaction.

The following compounds are prepared according to the procedure of Example 41 and 42.

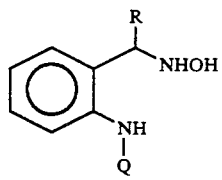

| Example No. | Q | R | mp °C. | % Yield | Prepared from Compound of Example | Prepared by Method of Example |
|---|---|---|---|---|---|---|
| 42 | 2,6-dichlorophenyl | H | oil | 91% | 38 | 42 |
| 43 | 2,6-dichloro-3-methylphenyl | H | oil | 43% | 39 | 41 |

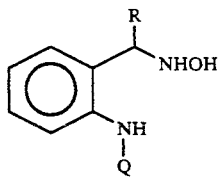

| Example No. | Q | R | mp °C. | % Yield | Prepared from Compound of Example | Prepared by Method of Example |
| --- | --- | --- | --- | --- | --- | --- |
| 44 | 3-CF₃-phenyl | H | oil | 70% | 40 | 42 |
| 45 | 2,6-dichloro-3-methyl-phenyl | Me | oil | 45% | 52 | 41 |

EXAMPLE 47

N-[(2-[(2,3-Dimethylphenyl)amino]phenyl]methyl-N-hydroxyacetamide

Acetyl chloride (0.53 g, 6.8 mmol) is added dropwise at 0° C. to a solution of 2-[(2,3-dimethylphenyl)amino]-N-hydroxybenzenemethanamine (1.64 g, 6.8 mmol) and sodium acetate (840 mg, 10 mmol) in 2:1 dioxane/water (100 ml). The reaction mixture is stirred at room temperature for 30 minutes. The product is extracted into ethyl acetate. The organic layer is washed with brine, dried over magnesium sulfate and evaporated to a residue which is recrystallized from cyclohexane to give pure N-[[2-[(2,3-dimethylphenyl)amino]phenyl]-methyl]-N-hydroxyacetamide (1.02 g, 53%); mp 93°–98° C.

Anal. Calcd for $C_{17}H_{20}N_2O_2$:
C, 71.81; H, 7.09; N, 9.85.
Found: C, 71.51; H, 6.93; N, 9.65.

EXAMPLE 48

N-[[(2,6-Dichlorophenyl)amino]phenyl]methyl-N-hydroxyacetamide

A solution of 2-[(2,6-dichlorophenyl)amino]-N-hydroxybenzenemethanamine (2.0 g, 7 mmol) and triethylamine (2.12 g, 21 mmol) in dichloromethane (100 ml) is treated with acetyl chloride (1.1 ml, 15.5 mmol) dropwise with stirring, under an argon atmosphere. The reaction mixture is stirred for 50 minutes at room temperature and then washed with water (3×200 ml). The solvent is evaporated and the residue recrystallized from hexane to give the crude intermediate bis-acetyl derivative which is dissolved with warming in isopropanol (200 ml). The solution is treated with a solution of lithium hydroxide (0.84 g, 35 mmol) in water (30 ml). The reaction mixture is stirred at room temperature for 30 minutes and is neutralized by the addition of 1N HCl. The reaction mixture is diluted with water (300 ml) and the product is extracted into ethyl acetate. The solvent is removed and the residue is recrystallized from isopropyl ether/ethyl acetate to give pure N-[[(2,6-dichlorophenyl)amino]phenyl]methyl-N-hydroxyacetamide (600 mg, 26%); mp 165°–171° C.

Anal. Calcd for $C_{15}H_{14}Cl_2N_2O_2$:
C, 55.40; H, 4.34; N, 8.61; Cl, 21.80.
Found: C, 55.20; H, 4.14; N, 8.43; Cl, 21.66.

EXAMPLE 49

1-[2-[(2,6-Dichloro-3-methylphenyl)amino]phenyl]-2-(methylsulfinyl)ethanone

2-[(2,6-Dichloro-3-methylphenyl)amino]benzoic acid methyl ester (3.3 g, 10.6 mmol) is dissolved in 30 ml of dry THF and added to a solution of dimsyl anion (JACS, 84, 866, 1982) (31.9 mmol) in 60 ml of 1:1 DMSO/THF at 0° C. under argon. When addition is complete, the ice bath is removed and the reaction mixture is stirred at room temperature for five hours. The reaction is quenched with 400 ml of 1N hydrochloric acid, and extracted twice with 300 ml of chloroform. The combined chloroform extract is washed with 300 ml of water three times, and once with 300 ml of brine. This chloroform layer is dried over magnesium sulfate and evaporated. The residue solidifies after being dried at room temperature under vacuum for 12 hours. Recrystallization from methylene chloride in hexane gives 1.0 g of 1-[2-[(2,6-dichloro-3-methylphenyl)amino]phenyl]-2-(methylsulfinyl)ethanone (26% yield); mp 152°–154° C.

Anal Calcd for $C_{16}H_{15}Cl_2NO_2S$:
C, 53.94; H, 4.25, N, 3.93, Cl, 19.90, S, 9.00.
Found: C, 54.00; H, 4.26; N, 3.91; Cl, 19.74; S, 8.93.

EXAMPLE 50

1-[2-[(2,6-Dichloro-3-methylphenyl)amino]phenyl]ethanone

1-[2-[(2,6-Dichloro-3-methylphenyl)amino]phenyl]-2-(methylsulfinyl)ethanone (2.0 g, 5.61 mmol) is dissolved in 100 ml of 10% water/tetrahydrofuran and cooled to 0° C. in an ice bath. Aluminum amalgam is prepared by addition of aluminum foil (1.5 g, 56.1 mmol) to 350 ml of 2% aqueous mercuric chloride. After 15 seconds, the liquid is decanted, and the foil is washed twice with absolute ethanol followed by tetrahydrofuran. The freshly prepared aluminum amalgam is added to the reaction mixture which is then stirred for 30 minutes at 0° C. The reaction mixture is filtered through celite, and the solids are washed with tetrahydrofuran. The filtrate is evaporated, and the residue is taken up in ether. The ether solution is washed with 100 ml of water and dried over magnesium sulfate. Evaporation of the solvent gives a yellow solid which is recrystallized from diethyl ether/hexane. Yield (1.0 g, 60%) of 1-[2-[(2,6-dichloro-3-methylphenyl)amino]phenyl]ethanone; mp 122°-125° C.

Anal. Calcd for $C_{15}H_{13}Cl_2NO$:
C, 61.24; H, 4.46; N, 4.76.
Found: C, 61.26; H, 4.51; N, 4.71.

EXAMPLE 51

1-[2-[(2,6-Dichloro-3-methylphenyl)amino]phenyl]ethanone

2-[(2,6-Dichloro-3-methylphenyl)amino]benzoic acid (8.4 g, 28.5 mmol) and carbonyl diimidazole (6.9 g, 42.7 mmol) are stirred in 300 ml THF under argon for two hours. Malonic acid monoethyl ester, magnesium salt (24.0 g, 85.4 mmol) is added and the reaction mixture is warmed to reflux for 15 hours. The solvent is evaporated, and the residue partitioned between ethyl acetate and 1N HCl. The pH of the aqueous layer is adjusted to pH=1 with concentrated HCl. The aqueous layer is extracted with ethyl acetate. The organic layer is washed with 1N HCl, and with saturated sodium bicarbonate, and then dried over magnesium sulfate and evaporated. The solid remaining is taken up in ethyl acetate and adsorbed onto a silica gel pad. The pad is washed with chloroform. Evaporation of the chloroform gives crude β-keto ester which is treated with 30% water/trifluoroacetic acid at reflux for two hours. The trifluoroacetic acid is evaporated, and the residue is taken up in diethyl ether. The ether solution is washed with 100 ml of saturated sodium bicarbonate three times. It is dried over magnesium sulfate, and evaporated. The remaining solid is taken up in methylene chloride and adsorbed onto a silica gel pad. This pad is washed with methylene chloride. Evaporation of the solvent gives a yellow solid. Recrystallization from methylene chloride/hexane gives 6.5 g (42%) of 1-[2-[(2,6-dichloro-3-methylphenyl) amino]phenyl]ethanone; mp 130°-132° C.

Anal. Calcd for $C_{15}H_{13}Cl_2NO$:
C 61.24; H, 4.46; N, 4.76.
Found: C, 61.09; H, 4.45; N, 4.74.

EXAMPLE 52

1-[2-[(2,6-Dichloro-3-methylphenyl)amino]phenyl]ethanone oxime

1-[2-[(2,6-Dichloro-3-methylphenyl)amino]phenyl]ethanone (0.8 g, 2.7 mmol) and hydroxylamine hydrochloride (0.8 g, 10.8 mmol) are dissolved in 15 ml of pyridine under argon at room temperature for 12 hours. The pyridine is evaporated, and the residue partitioned between methylene chloride and water. The organic layer is washed twice with 100 ml of water and dried over magnesium sulfate. The solution is concentrated on the rotovap and passed through a silica gel pad which is then eluted with methylene chloride. The solvent is evaporated and 1-[2-[(2,6-dichloro-3-methylphenyl)amino]phenyl]ethanone oxime is recrystallized from H₂O/MeOH. Yield 0.2 g (24%); mp 116°-118° C.

Anal. Calcd for $C_{15}H_{14}Cl_2N_2O$:
C, 58.26; H, 4.57; N, 9.06; Cl, 22.93.
Found: C, 58.32; H, 4.60; N, 8.82; Cl, 22.93.

EXAMPLE 53

N-[1-[2-[(2,6-Dichloro-3-methylphenyl)amino]phenyl]ethyl]-N-hydroxyacetamide

2-[(2,6-Dichloro-3-methylphenyl)amino]-N-hydroxy-α-methylbenzenemethanamine (1.2 g, 3.8 mmol) is reacted with acetyl chloride (0.66 g, 8.5 mmol), triethylamine (1.2 g, 11.6 mmol), and lithium hydroxide (0.46 g, 19.3 mmol) according to the procedure of Example 48 to give N-[1-[2-[(2,6-dichloro-3-methylphenyl) amino]phenyl]ethyl]-N-hydroxyacetamide (0.6 g, 45% yield); mp 185°-187° C.

Anal. Calcd for $C_{17}H_{18}Cl_2N_2O_2$:
C, 57.79; H, 5.15; N, 7.93; Cl, 20.07.
Found: C, 57.91; H, 5.00; N, 7.64; Cl, 20.13.

EXAMPLE 54

N-[[2-[(2,6-Dichloro-3-methylphenyl)amino]phenyl]methyl]-N-hydroxyacetamide

2-[(2,6-Dichloro-3-methylphenyl)amino]-N-hydroxybenzenemethanamine (1.00 g, 3.4 mmol) is reacted with acetyl chloride (0.58 g, 7.4 mmol), triethylamine (1.0 g, 10.1 mmol), and lithium hydroxide (0.40 g, 16.8 mmol) according to the procedure of Example 48 to give 0.5 g (43% yield) of N-[[2-[(2,6-dichloro-3-methylphenyl)amino]phenyl]methyl]-N-hydroxyacetamide; mp 155°-156° C.

Anal. Calcd for $C_{16}H_{16}Cl_2N_2O_2$:
C, 56.64; H, 4.76; N, 8.26; Cl, 20.90.
Found: C, 56.68; H, 4.61; N, 8.10; Cl, 21.39.

EXAMPLE 55

N-Hydroxy-N-[[2-[[3-(trifluoromethyl)phenyl]amino]phenyl]methylacetamide

2-[[3-(Trifluoromethyl)phenyl]amino]-N-hydroxybenzenemethanamine (2.0 g, 7.1 mmol) is reacted with sodium acetate (0.87 g, 10.6 mmol) and acetyl chloride (0.56 g, 7.1 mmol) according to the procedure of Example 47 to give 1.2 g (52% yield) of N-hydroxy-N-[[2-[[3-(trifluoromethyl)phenyl]amino]phenyl]methylacetamide; mp 124°-125° C.

Anal. Calcd for $C_{16}H_{15}F_3N_2O_2$:
C, 59.25; H, 4.67; N, 8.64; F, 17.57.
Found: C, 58.85; H, 4.73; N, 8.49; F, 17.69.

EXAMPLE 56

N-Hydroxy-N'-methyl-N-[[2-[[3-(trifluoromethyl) phenyl]amino]phenyl]methylurea

2-[[3-(Trifluoromethyl)phenyl]amino]-N-hydroxybenzenemethanamine (3.1 g, 11.0 mmol) is dissolved in 75 ml of 2:1 dioxane/water and cooled to −10° C. in an ice-salt water bath. Methyl isocyanate (1 eq) is added dropwise at −10° C, and the reaction mixture is kept at that temperature for 10 minutes. The reaction mixture is quenched with water and extracted with ethyl acetate. The ethyl acetate extract is washed with brine, and dried over magnesium sulfate. The solvent is evaporated, and N-hydroxy-N'-methyl-N-[[2-[[3-(trifluoromethyl) phenyl]amino]phenyl]methylurea is recrystallized from methylene chloride in hexane. Yield 1.1 g, 29%; mp 138°-139° C.

Anal. Calcd for $C_{16}H_{16}F_3N_3O_2$
C, 56.63; H, 4.76; N, 12.39; F, 16.8.

Found C, 56.61; H, 4.77; N, 12.27; F, 16.78.

EXAMPLE 57

N-Hydroxy-N-[[2-[[3-(trifluoromethyl)phenyl]amino]-phenyl]methyl]carbamic acid, ethyl ester 2-[[3-(Trifluoromethyl)phenyl]amino]-N-hydroxybenzenemethanamine is reacted with ethyl chloroformate according to the procedure of Example 47 to obtain N-hydroxy-N-[2-[[3-(trifluoromethyl)phenyl]amino]methyl]carbamic acid, ethyl ester; mp 82°–84° C.

EXAMPLE 58

5-Methoxy-2-methyl-1H-indole-3-carboxaldehyde

Phosphorous oxychloride (12.7 ml, 0.136 mol) is added dropwise at 0° C. to dimethylformamide (42.4 ml, 0.544 mol) over 30 minutes. A solution of 5-methoxy-2-methylindole (20 g, 0.124 mol) in 40 ml of DMF is added dropwise over 45 minutes. When 30 ml of the indole solution has been added, it becomes necessary to add 10 ml of DMF to break up the heavy paste which forms. The reaction mixture is then warmed to 35° C. for one hour. After 30 minutes the reaction again becomes too pasty, and 5 ml more of DMF is added. The bath is removed, and 60 g of crushed ice is added quickly to the reaction mixture. The reaction mixture is stirred for 30 minutes followed by addition of 20 ml of water and 40 g of ice. A solution of sodium hydroxide (25 g) in water (200 ml) is added dropwise to the red solution. After the first one-third of this sodium hydroxide solution has been added, the color changes to yellow, and the remainder of the sodium hydroxide solution is added quickly. It is rapidly brought to a boil (100°–120° C.) for 10 minutes, cooled and refrigerated overnight. The solid is filtered and washed four times with cool water. It is dried in a vacuum oven at 50° C. for 22 hours to give 23.0 g (98%) of powdery yellow crystals of pure 5-methoxy-2-methyl-1H-indole-3-carboxaldehyde; mp 190°–191° C.

Anal. Calcd for $C_{11}H_{11}NO_2$:
C, 69.83; H, 5.86; N, 7.40.
Found: C, 69.48; H, 5.87; N, 7.41.

EXAMPLE 59

1-(4-Chlorobenzoyl)-5-methoxy-2-methyl-1H-indole-3-carboxaldehyde

To a solution of 5-methoxy-2-methyl-1H-indole-3-carboxaldehyde (20 g, 106 mmol) in 210 ml of dry dimethylformamide is added oil free sodium hydride (2.7 g, 111 mmol). The reaction mixture is stirred for five hours at which time it is cooled to −60° C., and freshly distilled 4-chlorobenzoyl chloride (14.4 ml, 117 mmol) is added dropwise. It is stirred for an additional 10 minutes and worked up by pouring the cold paste into cold ethyl acetate and water. The organic phase is washed once with dilute sodium bicarbonate solution, once again with water, and once with a saturated solution of sodium chloride. It is further dried with magnesium sulfate, filtered, and concentrated in vacuo to a solid which is stirred vigorously with 50 ml of methanol for two hours. The solid is filtered and dried to give 1-(4-chlorobenzoyl)-5-methoxy-2-methyl-1H-indole-3-carboxaldehyde (28.7 g, 82.5%). A portion which is recrystallized from ethyl acetate has a mp of 150.5°–151.5° C.

Anal. Calcd for $C_{18}H_{14}ClNO_3$:
C, 65.96; H, 4.31; N, 4.27; Cl, 10.82.
Found: C, 65.87; H, 4.28; N, 4.16; Cl, 10.54.

EXAMPLE 60

1-(4-Chlorobenzoyl)-5-methoxy-2-methyl-1H-indole-3-carboxaldehyde, oxime

To a solution of 1-(4-chlorobenzoyl)-5-methoxy-2-methyl-1H-indole-3-carboxaldehyde (5.9 g, 18 mmol) in 90 ml of freshly distilled tetrahydrofuran at 0° C. is added anhydrous sodium acetate (4.4 g, 54 mmol) and anhydrous hydroxylamine hydrochloride (2.0 g, 28.8 mmol). After five minutes the ice bath is removed, and the reaction mixture is stirred for three hours. The reaction mixture is diluted with ethyl acetate and water. The pH of the aqueous layer is adjusted to pH=3-4 with dilute HCl. The organic layer is washed once with 10% sodium bicarbonate, once with water, and finally with a saturated solution of sodium chloride. It is further dried over magnesium sulfate, filtered, and concentrated in vacuo. The residue is purified by column chromatography (silica gel, 1:9 ethyl acetate:methylene chloride) to give 4.17 g (68%) of 1-(4-chlorobenzoyl)-5-methoxy-2-methyl-1H-indole-3-carboxaldehyde, oxime. A sample which is recrystallized from tetrahydrofuran:methanol:water Anal. Calcd for $C_{18}H_{15}ClN_2O_3$:
C, 63.07; H, 4.41; N, 8.17
Found C, 62.85; H, 4.34; N, 8.01.

EXAMPLE 61

1-(4-Chlorobenzoyl)-N-hydroxy-5-methoxy-2-methyl-1H-indole-3-methanamine

To a suspension of 1-(4-chlorobenzoyl)-5-methoxy-2-methyl-1H-indole-3-carboxaldehyde, oxime (1.0 g, 2.9 mmol) in 15 ml of acetic acid is added 0.9 g (14.6 mmol) of sodium cyanoborohydride (0.9 g, 14.6 mmol). The reaction mixture is stirred vigorously for three hours whereupon an additional 0.35 g (5.6 mmol) of the reducing agent is added. After an additional 45 minutes the reaction mixture is diluted with ethyl acetate and methylene chloride, cooled to 0° C., and 300 ml of a saturated solution of sodium bicarbonate is added dropwise while continuing to stir vigorously. This mixture is diluted further with 400 ml of ethyl acetate and separated from the aqueous phase (pH=9). The organic phase is washed again with a saturated solution of sodium bicarbonate, water, and finally a saturated solution of sodium chloride. It is dried over magnesium sulfate, filtered, and concentrated to a yellow oil which is crude 1-(4-chlorobenzoyl)-N-hydroxy-5-methoxy-2-methyl-1H-indole-3-methanamine and is used without further purification in the subsequent reaction. Mass balance is quantitative. A sample recrystallized from methylene chloride has a mp of 164°–165° C. (dec).

Anal. Calcd for $C_{18}H_{17}ClN_2O_3$:
C, 62.70; H, 4.97; N, 8.12; Cl, 10.28.
Found: C, 62.01; H, 4.90; N, 7.96; Cl, 10.99.

EXAMPLE 62

N-[[1-(4-Chlorobenzoyl)-5-methoxy-2-methyl-1H-indole-3-yl]methyl]-N-hydroxyacetamide To a suspension of 1-(4-chlorobenzoyl)-N-hydroxy-5-methoxy-2-methyl-1H-indole-3-methanamine (1,2 g, 3.5 mmol) and sodium acetate (730 mg, 8.9 mmol) in 120 ml of 1,4-dioxane and 30 ml of water is added dropwise acetyl chloride (420 μl, 5.9 mmol) at 0° C. After 10 minutes additional acetyl chloride (40 ul, 0.6 mmol) is added. The reaction mixture is stirred for 15 minutes, and then is diluted with ethyl acetate. It is washed once with a dilute solution of sodium bicarbonate, once with water, and a saturated solution of sodium chloride The organic phase is further dried over magnesium sulfate, filtered, and concentrated in vacuo. The residue is purified by column chromatography on silica gel, eluting first with 1:4 ethyl acetate:methylene chloride then 1:1 ethyl acetate:methylene chloride. Recrystallization from isopropyl ether gives N-[[1-(4-chlorobenzoyl)-5-methoxy-2-methyl-1H-indol-3-yl]methyl]-N-hydroxy-acetamide (645 mg, 47%); mp 160°-161° C.

Anal. Calcd for $C_{18}H_{17}ClN_2O_3$:
C, 62.10; H, 4.95; N, 7.24; Cl, 9.16.
Found: C, 61.98; H, 4.79; N, 6.99; Cl, 9.35.

EXAMPLE 63

3-[[[1-(4-Chlorobenzoyl)-5-methoxy-2-methyl-1H-indol-3-yl]methyl]hydroxyamino]-3-oxo-propanoic acid, ethyl ester According to the procedure of Example 62, 1-(4-chlorobenzoyl)-N-hydroxy-5-methoxy-2-methyl-1H-indole-3-methanamine is reacted with 1.1 eq of ethyl malonyl chloride in dioxane/water (1:1) in the presence of sodium acetate (2.5 eq). The crude product is purified by column chromatography (silica gel, 3:7 acetone:hexane). The product crystallizes from the chromatography solvents upon standing to give pure 3-[[[1-(4-chlorobenzoyl)-5-methoxy-2-methyl-1H-indol-3-yl]methyl]hydroxyamino]-3-oxopropanoic acid, ethyl ester (24%); mp 170°-171° C. dec.

Anal. Calcd for $C_{23}H_{23}ClN_2O_6$:
C, 60.20; H, 5.05; N, 6.10; Cl, 7.72
Found: C, 59.80; H, 5.03; N, 5.95; Cl, 8.24

EXAMPLE 64

4-[[[1-(4-Chlorobenzoyl)-5-methoxy-2-methyl-1H-indol-3-yl]methyl]hyiroxyamino]-4-oxo-butanoic acid, methyl ester According to the procedure of Example 62, 1-(4-chlorobenzoyl)-N-hydroxy-5-methoxy-2-methyl-1H-indole-3-methanamine is reacted with 2.1 eq of 3-carbomethoxypropionyl chloride in dioxane/water (1:1) in the presence of sodium acetate (2.5 eq). The crude product is purified by column chromatography (silica gel, 1:4 ethyl acetate:methylene chloride). The resulting product is slurried in ethyl acetate and filtered to give pure 4-[[[1-(4-chlorobenzoyl)-5-methoxy-2-methyl-1H-indol-3-yl]methyl]hydroxyamino]-4-oxo-butanoic acid, methyl ester (24%); mp 157.5°-158° C.

Anal Calcd for $C_{23}H_{23}ClN_2O_6$:
C, 60.20; H, 5.05; N, 6.10; Cl, 7.72.
Found: C, 60.48; H, 5.03; N, 5.98; Cl, 7.92.

EXAMPLE 65

4-[[[1-(4-Chlorobenzoyl)-5-methoxy-2-methyl-1H-indol-3-yl]methyl]hydroxyamino]-4-oxo-butanoic acid According to the procedure of Example 62, 1-(4-chlorobenzoyl)-N-hydroxy-5-methoxy-2-methyl-1H-indole-3-methanamine is reacted with 1.0 eq of succinic anhydride in dioxane/water (2:1) in the presence of sodium acetate (2.5 eq). The reaction mixture is diluted with ethyl acetate and is washed with dilute aqueous HCl and then with water. The crude product is purified by recrystallization from methylene chloride. The compound is dissolved in a minimal amount of methanol, diluted with water and lyophylized to give pure 4-[[[1-(4-chlorobenzoyl)-5-methoxy-2-methyl-1H-indol-3-yl]methyl]hydroxyamino]-4-oxo-butanoic acid (44%); mp 134°-136° C.

Anal. Calcd for $C_{22}H_{21}ClN_2O_6 \cdot 1.3H_2O$:
C, 56.42; H, 4.95; N, 5.98
Found: C, 56.45; H, 4.85; N, 5.83.

EXAMPLE 66

[[1-(4-Chlorobenzoyl)-5-methoxy-2-methyl-1H-indol-3yl]methyl]hydroxycarbamic acid, methyl ester According to the procedure of Example 62, 1-(4-chlorobenzoyl)-N-hydroxy-5-methoxy-2-methyl-1H-indole-3-methanamine is reacted with 1.1 eq of methyl chloroformate in dioxane/water (2:1) in the presence of sodium acetate (2.5 eq). The crude product is recrystallized from isopropyl ether:cyclohexane to give pure [[1-(4-chlorobenzoyl)-5-methoxy-2-methyl-1H-indol-3-yl]methyl]hydroxycarbamic acid, methyl ester (63%); mp 113°-114° C.

Anal. Calcd for $C_{20}H_{19}ClN_2O_5$:
C, 59.63; H, 4.75; N, 6.95; Cl, 8.80.
Found: C, 59.74; H, 4.73; N, 6.89; Cl, 7.61.

EXAMPLE 67

N-(Aminocarbonyl)-1-(4-chlorobenzoyl)-N-hydroxy-5-methoxy-2-methyl-1H-indole-3-methanamine To a suspension of 1-(4-chlorobenzoyl)-N-hydroxy-5-methoxy-2-methyl-1H-indole-3-methanamine (500 mg, 1.45 mmol) in 30 ml of 1,4-dioxane and 15 ml of water at 0° C. is added sodium isocyanate (104 mg, 1.59 mmol) followed by 1.59 ml (1.59 mmol) of 1N hydrochloric acid. The reaction mixture is diluted with ethyl acetate and washed once with water, and finally with a saturated solution of sodium chloride. It is further dried over magnesium sulfate, filtered, and concentrated in vacuo. The crude residue is recrystallized from methylene chloride and dried to give 300 mg (53%) of pure N-(aminocarbonyl)-1-(4-chlorobenzoyl)-N-hydroxy-5-methoxy-2-methyl-1H-indole -3-methanamine (535); mp 151.5°-154° C. dec.

Anal. Calcd for $C_{19}H_{18}ClN_3O_4$:
C, 58.84; H, 4.68; N, 10.83; Cl, 9.14.
Found: C, 58.60; H, 4.70; N, 10.72; Cl, 9.59.

EXAMPLE 68

1-(4-Chlorobenzoyl)-N-hydroxy-5-methoxy-2-methyl-N-[(methylamino)carbonyl]-1H-indole-3-methanamine According to the procedure of Example 62, 1-(4-chlorobenzoyl)-N-hydroxy-5-methoxy-2-methyl-1H-indole-3-methanamine is reacted with 1.1 eq of methyl isocyanate in dioxane/water (2:1) in the absence of sodium acetate. The crude product is purified by column chromatography (silica gel) eluting with a gradient of acetone/hexane to give pure 1-(4-chlorobenzoyl)-N-hydroxy-5-methoxy-2-methyl-N-[(methylamino)carbonyl]-1H-indole-3-methanamine (51%) as an amorphous solid.

Anal. Calcd for $C_{20}H_{20}ClN_3O_4$:
C, 59.78; H, 5.02; N, 10.46; Cl, 9.82.
Found: C, 59.64; H, 5.05; N, 10.21; Cl, 9.54.

EXAMPLE 69

1-(4-Chlorobenzoyl)-N-[(dimethylamino)carbonyl]-N-hydroxy-5-methoxy-2-methyl-1H-indole-3-methanamine According to the procedure of Example 62, 1-(4-chlorobenzoyl)-N-hydroxy-5-methoxy-2-methyl-1H-indole-3-methanamine is reacted with 14 eq of dimethylcarbamoyl chloride and 3.5 eq of sodium acetate (added in portions). The crude product is purified by column chromatography (silica gel, 1:4/ethyl acetate:-methylene chloride). Recrystallization from methylene chloride:hexane, followed by column chromatography (silica gel, ether) and recrystallization from methanol:-water gives pure 1-(4-chlorobenzoyl)-N-[(dimethylamino)carbonyl]-N-hydroxy-5-methoxy-2-methyl-1H-indole-3-methanamine (30%); mp 173°-174° C.

Anal. Calcd for $C_{21}H_{22}ClN_3O_4$:
C, 60.65; H, 5.33; N, 10.10; Cl, 8.52.
Found: C, 60.90; H, 5.21; N, 9.95; Cl, 8.56.

EXAMPLE 70

1-(4-Chlorobenzoyl)-N-hydroxy-5-methoxy-2-methyl-N-[(2-propenylamino)carbonyl]-1H-indole-3-methanamine According to the procedure of Example 62, 1-(4-chlorobenzoyl)-N-hydroxy-5-methoxy-2-methyl-1H-indole-3-methanamine is reacted with 1.2 eq of allyl isocyanate in dioxane/water (1:1) in the presence of sodium acetate (2.5 eq). The crude product is purified by column chromatography (silica, 3:7 ethyl acetate:-methylene chloride). Recrystallization from methylene chloride:hexane, and then from methanol:water gives pure 1-(4-chlorobenzoyl)-N-hydroxy-5-methoxy-2-methyl-N-[(2-propenylamino) carbonyl]-1H-indole-3-methanamine (44%); mp 148°-149° C.

Anal. Calcd for $C_{22}H_{22}ClN_3O_4$:
C, 61.76; H, 5.18; N, 9.82; Cl, 8.28.
Found: C, 61.59; H, 5.17; N, 9.59; Cl, 8.33.

EXAMPLE 71

[[[[1-(4-Chlorobenzoyl)-5-methoxy-2-methyl-1H-indol-3-yl]methyl]hydroxyamino]carbonyl]carbamic acid, ethyl ester To a solution of 1-(4-chlorobenzoyl)-N-hydroxy-5-methoxy-2-methyl-1H-indole-3-methanamine (540 mg, 1.57 mmol) in 30 ml of freshly distilled tetrahydrofuran at 0° C. is added dropwise 194 μl (1.88 mmol) of ethoxycarbonyl isocyanate. The reaction mixture is stirred for 10 minutes at 0° C. and concentrated in vacuo. The residue is purified by column chromatography on silica using an ethyl acetate:methylene chloride gradient (15:85 to 1:1). Recrystallization from methylene chloride:hexane gives pure [[[[1-(4-chlorobenzoyl)-5-methoxy-2-methyl-1H-indol-3-yl]methyl]hydroxyamino]carbonyl]carbamic acid, ethyl ester (68%); mp 147.5°-148° C.

Anal. Calcd for $C_{22}H_{22}ClN_3O_6$:
C, 57.46; H, 4.82; N, 9.14; Cl, 7.71
Found: C, 57.31; H, 4.87; N, 8.99; Cl, 7.77.

EXAMPLE 72

N-[[[1-(4-Chlorobenzoyl)-5-methoxy-2-methyl-1H-indol-3-yl]methyl]hydroxyamino]carbonyl]glycine, ethyl ester According to the procedure of Example 71, (1-(4-chlorobenzoyl)-N-hydroxy-5-methoxy-2-methyl-1H-indole-3-methanamine is reacted with ethyl isocyanatoacetate. The crude product is purified by column chromatography (silica gel, 1:4 ethyl acetate:methylene chloride) to give pure N-[[[[1-(4-chlorobenzoyl)-5-methoxy-2-methyl-1H-indol-3-yl]methyl]hydroxyamino]carbonyl]glycine, ethyl ester (27%) as an amorphous solid.

Anal. Calcd for $C_{23}H_{24}ClN_3O_6$:
C, 58.29; H, 5.10; N, 8.87; Cl, 7.48.
Found: C, 58.02; H, 5.03; N, 8.74; Cl, 7.98.

EXAMPLE 73

1-(4-Chlorobenzoyl)-N-hydroxy-5-methoxy-2-methyl-N-[(methylamino)thioxomethyl]-1H-indole-3-methanamine A solution of methyl isothiocyanate (1.36 g, 18.56 mmol) in 2 ml of dioxane is added dropwise to a suspension of 1-(4-chlorobenzoyl)-N-hydroxy-5-methoxy-2-methyl-1H-indole-3-methanamine (2.01 g, 5.84 mmol) in 60 ml of dioxane and 60 ml of H20 at 0° C. The ice bath is removed. After one hour 0.5 g (6.84 mmol) additional methyl isothiocyanate is added and the reaction mixture is stored in a freezer overnight. The solids are collected by filtration and recrystallized from THF/hexane, rinsed with ether, and dried under high vacuum over $P_2O_5$ to give pure 1-(4-chlorobenzoyl)-N-hydroxy-5-methoxy-2-methyl-N-[(methylamino)thioxomethyl]-1H-indole-3-methanamine (1.32 g, 54%); mp 198°-198.5° C. (dec).

Anal. Calcd for $C_{20}H_{20}ClN_3O_3S$:
C, 57.48; H, 4.82; N, 10.05; Cl, 8.48
Found: C, 57.72; H, 4.80; N, 9.67; Cl, 8.57.

EXAMPLE 74

1-(5-Methoxy-2-methyl 1H-indol-3-yl)ethanone

Dimethylacetamide (17.5 ml, 188.4 mmol) is added dropwise with stirring to phosphorous oxychloride (12.9 ml, 138.2 mmol) at 0° C. Stirring is maintained for 45 minutes, at which time the bath is removed and 5-methoxy-2-methylindole (20.25 g, 125.6 mmol) in 15 ml of dimethylacetamide is added dropwise over a period of 75 minutes. The resulting mixture is warmed to 40°-45° C. for 4 hours. The reaction mixture is cooled to 0° C., and 100 g of ice water is added followed by dropwise addition of a solution of sodium hydroxide (50 g) in water (75 ml). The first ⅓ of this sodium hydroxide solution is added slowly and the remainder is added quickly. The exothermic reaction is quickly warmed to boiling for 15 minutes, cooled to room temperature and refrigerated overnight. The resulting crystals are collected by filtration and rinsed four times with water. Recrystallization from ethanol/water gives 17.2 g (67.2%) of pure 1-(5-methoxy-2-methyl-1H-indol-3-yl)ethanone; mp 229.0°-230.5° C.

Anal. Calcd for $C_{12}H_{13}NO_2$:
C, 70.92; H, 6.45; N, 6.89.
Found: C, 70.92; H, 6.55; N, 6.86.

EXAMPLE 75

(5-Methoxy-2-methyl-1H-indol-3-yl)ethanone, O-(tetrahydro-2H-pyran-2-yl)oxime

To a suspension of of 1-(5-methoxy-2-methyl-1H-indol-3-yl)ethanone (17.2 g, 84.6 mmol) and anhydrous pyridinium hydrochloride (4.9 g, 42.3 mmol) in dry pyridine (200 ml) is added dropwise a solution of O-tetrahydropyranyl hydroxylamine (9.9 g, 84.6 mmol) in dry pyridine (200 ml) and the reaction mixture is stirred at room temperature overnight. An additional 3.0 g (25.6 mmol) of O-tetrahydropyranyl hydroxylamine is added and the reaction mixture is stirred at room temperature overnight. It is concentrated in vacuo to about ¼ volume, diluted with ethyl acetate and washed four times with water and once with a saturated solution of sodium chloride. The organic layer is dried over magnesium sulfate, filtered, and slowly concentrated in vacuo to give a total of 23.3 g (91.5%) (from three crops) of crystalline (5-methoxy-2-methyl-1H-indol-3-yl)ethanone, O-(tetrahydro-2H-pyran-2-yl)oxime; mp 156.5°–157.5° C.

Anal. Calcd for $C_{17}H_{22}N_2O_3$:
C, 67.53; H, 7.33; N, 9.26.
Found: C, 67.55; H, 7.44; N, 9.26.

EXAMPLE 76

1-(4-Chlorobenzoyl)-5-methoxy-2-methyl-3-[1-[[(tetrahydro-2H-pyran-2-yl) oxy]imino]ethyl]-1H-indole To a solution of (5-methoxy-2-methyl-1H-indol-3-yl)ethanone, O-(tetrahydro-2H-pyran-2-yl)oxime (23.3 g, 77.3 mmol) in dry dimethylformamide (500 ml) is added oil free sodium hydride (2.0 g, 83.3 mmol). The reaction mixture is stirred for four hours at ambient temperature. It is cooled to 0° C. and freshly distilled 4-chlorobenzoyl chloride is added dropwise over 15 minutes. The reaction mixture is stirred for an additional hour, at which time it is diluted with ethyl acetate and water and the aqueous layer acidified to pH=3 with 1N hydrochloric acid. The organic layer is washed four additional times with large volumes of water. The organic phase is dried by washing with a saturated solution of sodium chloride and then over magnesium sulfate. It is filtered and concentrated in vacuo to an amorphous solid which is recrystallized from hot isopropyl ether to give 26.9 g (79.1%) of 1-(4-chlorobenzoyl)-5-methoxy-2-methyl-3-[1-[[(tetrahydro -2H-pyran-2-yl)oxy]imino]ethyl]-1H-indole; mp 115°–119° C.

Anal. Calcd for $C_{24}H_{25}ClN_2O_4$:
C, 65.38; H, 5.71; Cl, 8.04; N, 6.35;
Found: C, 65.06; H, 5.61; Cl, 8.34; N, 5.95.

EXAMPLE 77

1-(4-Chlorobenzoyl)-3-[1-(hydroxyimino)ethyl]-5-methoxy-2-methyl-1H-indole

To a solution of 1-(4-chlorobenzoyl)-5-methoxy-2-methyl -3-[1-[[(tetrahydro-2H-pyran-2-yl)oxy]imino]ethyl]-1H-indole (5.0 g, 11.3 mmol) in tetrahydrofuran (115 ml) is added 10 ml of concentrated hydrochloric acid. The reaction mixture is stirred for 2½ hours, at which time it is neutralized with concentrated ammonium hydroxide. It is concentrated to near dryness, diluted with ethyl acetate and washed twice with water and once with a saturated solution of sodium chloride. The organic phase is further dried over magnesium sulfate, filtered, and concentrated slowly in vacuo to 50 ml. The powdery crystals are collected to give 2.8 g (70.4%) of pure 1-(4-chlorobenzoyl)-3-[1-(hydroxyimino)ethyl]-5-methoxy-2-methyl-1H-indole; mp darkens (chars) at 170°–197° C. (dec).

Anal. Calcd for $C_{19}H_{17}ClN_2O_3$:
C, 63.96; H, 4.80; Cl, 9.94; N, 7.8.
Found: C, 63.71; H, 4.82; Cl, 10.06; N, 7.64.

EXAMPLE 78

1-(4-Chlorobenzoyl)-3-[1-(hydroxyamino)ethyl]-5-methoxy-2-methyl-1H-indole

To a solution of 1-(4-chlorobenzoyl)-3-[1-(hydroxyamino)ethyl]-5-methoxy-2-methyl-1H-indole (1.0 g, 2.80 mmol) in acetic acid (30 ml) is added methyl orange indicator and three drops of concentrated hydrochloric acid. Eight portions of 300 mg (4.80 mmol) of sodium cyanoborohydride is added every 30 minutes. The reaction mixture is diluted with 50 ml of ethyl acetate and 25 ml of methylene chloride, cooled to 0°, and quenched with 500 ml of a saturated solution of sodium bicarbonate added dropwise. It is then further diluted with 500 ml of ethyl acetate, and the phases are separated. The organic layer is extracted again with a saturated solution of sodium bicarbonate, once with water, and once with a saturated solution of sodium chloride. It is further dried over magnesium sulfate, filtered, and concentrated in vacuo to 2 ml. The addition of 2 ml of methylene chloride precipitates 500 mg of starting oxime. The mother liquor is concentrated to crude 1-(4-chlorobenzoyl)-3-[1-(hydroxyamino)ethyl]-5-methoxy-2-methyl-1H-indole as a yellow oil which is used without further purification in the subsequent reaction. A sample recrystallized from methylene chloride has a mp of 179°–180° C. (dec).

Anal. Calcd for $C_{19}H_{19}ClN_2O_3$:
C, 63.60; H, 5.34; N, 7.81.
Found: C, 61.85; H, 5.22; N, 7.61.

EXAMPLE 79

N-[1-[1-(4-Chlorobenzoyl)-5-methoxy-2-methyl-1H-indol-3-yl]ethyl]-N-hydroxyacetamide To a solution of 500 mg of 1-(4-chlorobenzoyl)-3-[1-(hydroxyamino)ethyl]-5-methoxy-2-methyl-1H-indole (crude product of Example 78) and 230 mg (2.8 mmol) of sodium acetate in 20 ml of 1,4-dioxane and 5 ml of water is added dropwise 90 μl (1.26 mmol) of acetyl chloride. The reaction mixture is stirred for 10 minutes, at which time it is diluted with ethyl acetate and washed twice with water and once with a saturated solution of sodium chloride. The organic phase is further dried over magnesium sulfate, filtered, and concentrated in vacuo. The residue is purified by column chromatography, eluting with a gradient of ethyl acetate:methylene chloride (3:7 to 1:1). A second chromatography (silica gel, ether), and finally recrystallization from methanol gives 71 mg (6.3% from oxime) of pure N-[1-[1-(4-chlorobenzoyl) -5-methoxy-2-methyl-1H-indol-3-yl]ethyl]-N-hydroxyacetamide; mp softens at 90° C. then decomposes as the temperature increases.

Anal. Calcd for $C_{21}H_{21}ClN_2O_4$:
C, 62.92; H, 5.28; N, 6.99; Cl, 8.84.
Found: C, 63.26; H, 5.37; N, 6.64; Cl, 9,35.

We claim:

1. A compound of the formula (I)

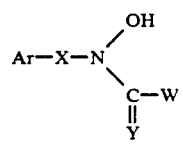

and a pharmaceutically acceptable acid addition or base salt thereof; wherein

Ar is

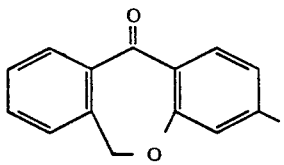

X is $CH_2$,

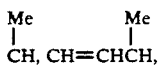

or $CH=CHCH_2$;

Y is O or S;

W is lower alkyl, aryl, aralkyl, lower alkoxy, $NR_6R_7$, $(CH_2)_nCO_2R_7$, $NH(CH_2)_mCO_2R_7$, $NH(CH_2)_pNR_6R_7$, or $NHCH_2CH=CH_2$ $R_6$ and $R_7$ are independently hydrogen or lower alkyl, n is an integer of from 0 to 3, m is an integer of from 0 to 3; and p is an integer of 2 or 3;

with the proviso that Y cannot be sulfur when n is 0.

2. A compound of claim 1 wherein X is a $CH_2$, or $$\overset{Me}{\underset{|}{CH.}}$$

3. A compound of claim 1 wherein X is $CH=CHCH_2$ or $$CH=CH\overset{Me}{\underset{|}{CH}}.$$

4. A compound of claim 1 wherein Y is oxygen.

5. A compound of claim 1 wherein Y is sulfur.

6. A compound of claim 1 which is N-[(6,11-dihydro-11-oxodibenz[b,e]oxepin-3-yl)methyl]-N-hydroxy-2-methylpropanamide.

7. A compound of claim 1 which is
N-[(6,11-dihydro-11-oxodibenz[b,e]oxepin-3-yl(methyl]-N-hydroxyacetamide,
[[(6,11-dihydro-11-oxodibenz[b,e]oxepin-3-yl)methyl]-hydroxyamino]oxoacetic acid, ethyl ester, or
N-[(6,11-dihydro-11-oxodibenz[b,e]oxepin-3-yl)methyl]-N-hydroxy-N'-methylurea.

8. A pharmaceutical composition for use as an antiinflammatory agent comprising an antiinflammatory amount of the compound of claim 1 and a pharmaceutical carrier.

9. A method of treating inflammation in a mammal suffering therefrom which comprises administering the compound of claim 1 in unit dosage form.

* * * * *